US011247006B2

United States Patent
Novak, III et al.

(10) Patent No.: US 11,247,006 B2
(45) Date of Patent: *Feb. 15, 2022

(54) CARTRIDGE AND CONTROL BODY OF AN AEROSOL DELIVERY DEVICE INCLUDING ANTI-ROTATION MECHANISM AND RELATED METHOD

(71) Applicant: RAI Strategic Holdings, Inc., Winston-Salem, NC (US)

(72) Inventors: Charles Jacob Novak, III, Winston-Salem, NC (US); Michael Ryan Galloway, Winston-Salem, NC (US); John DePiano, Burlington, MA (US); Frank S. Silveira, Wilmington, MA (US); Frederic Philippe Ampolini, Winston-Salem, NC (US); Michael Laine, Newburyport, MA (US); Raymond Charles Henry, Cary, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 72 days.

This patent is subject to a terminal disclaimer.

(21) Appl. No.: 16/662,617

(22) Filed: Oct. 24, 2019

(65) Prior Publication Data

US 2020/0054078 A1 Feb. 20, 2020

Related U.S. Application Data

(60) Division of application No. 15/434,963, filed on Feb. 16, 2017, now Pat. No. 10,492,532, which is a
(Continued)

(51) Int. Cl.
*A24F 47/00* (2020.01)
*A61M 15/06* (2006.01)
(Continued)

(52) U.S. Cl.
CPC ............ *A61M 15/06* (2013.01); *A24F 40/40* (2020.01); *A24F 40/50* (2020.01); *A61M 11/042* (2014.02);
(Continued)

(58) Field of Classification Search
CPC ....................................................... A24F 40/40
See application file for complete search history.

(56) References Cited

U.S. PATENT DOCUMENTS 1,771,366 A 7/1930 Wyss et al.
2,057,353 A 10/1936 Whittemore, Jr.
(Continued)

FOREIGN PATENT DOCUMENTS

AU 276250 7/1965
CA 2 641 869 5/2010
(Continued)

OTHER PUBLICATIONS

International Search Report and Written Opinion of the International Searching Authority for corresponding International Application No. PCT/US2014/024815 dated Oct. 8, 2014.
(Continued)

*Primary Examiner* — Eric Yaary
(74) *Attorney, Agent, or Firm* — Womble Bond Dickinson (US) LLP

(57) ABSTRACT

The present disclosure relates to aerosol delivery devices including a cartridge and a control body. The control body may include a coupler and the cartridge may include a base. The base may be configured to releasably engage the cartridge. Further the base and the coupler may include anti-rotation mechanisms configured to prevent rotation of the cartridge relative to the base when engaged with one
(Continued)

another. The anti-rotation mechanisms may include alternating protrusions and recesses in some embodiments. Related methods are also provided.

6 Claims, 18 Drawing Sheets

Related U.S. Application Data continuation of application No. 13/840,264, filed on Mar. 15, 2013, now Pat. No. 9,609,893.

(51) Int. Cl.
*H05B 3/00* (2006.01)
*A61M 11/04* (2006.01)
*A24F 40/40* (2020.01)
*A24F 40/50* (2020.01)
*H05B 3/46* (2006.01)
*A61M 16/00* (2006.01)
*A24F 40/10* (2020.01)

(52) U.S. Cl.
CPC ............... *H05B 3/00* (2013.01); *H05B 3/46* (2013.01); *A24F 40/10* (2020.01); *A61M 2016/0039* (2013.01); *A61M 2205/3653* (2013.01); *A61M 2205/584* (2013.01); *A61M 2205/8206* (2013.01); *H05B 2203/021* (2013.01); *Y10T 29/49002* (2015.01)

(56) References Cited

U.S. PATENT DOCUMENTS

| | | |
|---|---|---|
| 2,104,266 A | 1/1938 | McCormick |
| 2,174,531 A | 10/1939 | Robinson |
| 2,599,485 A | 6/1952 | Robinson |
| 2,805,669 A | 9/1957 | Meriro |
| 3,200,819 A | 8/1965 | Gilbert |
| 3,316,919 A | 5/1967 | Green et al. |
| 3,398,754 A | 8/1968 | Tughan |
| 3,419,015 A | 12/1968 | Wochnowski |
| 3,424,171 A | 1/1969 | Rooker |
| 3,476,118 A | 11/1969 | Luttich |
| 4,054,145 A | 10/1977 | Berndt et al. |
| 4,131,117 A | 12/1978 | Kite et al. |
| 4,150,677 A | 4/1979 | Osborne |
| 4,190,046 A | 2/1980 | Virag |
| 4,219,032 A | 8/1980 | Tabatznik et al. |
| 4,253,684 A | 3/1981 | Tolbert et al. |
| 4,259,970 A | 4/1981 | Green, Jr. |
| 4,284,089 A | 8/1981 | Ray |
| 4,303,083 A | 12/1981 | Burruss, Jr. |
| 4,449,541 A | 5/1984 | Mays et al. |
| 4,506,682 A | 3/1985 | Muller |
| 4,635,651 A | 1/1987 | Jacobs |
| 4,674,519 A | 6/1987 | Keritsis et al. |
| 4,708,151 A | 11/1987 | Shelar |
| 4,714,082 A | 12/1987 | Banerjee et al. |
| 4,735,217 A | 4/1988 | Gerth et al. |
| 4,756,318 A | 7/1988 | Clearman et al. |
| 4,771,795 A | 9/1988 | White et al. |
| 4,771,796 A | 9/1988 | Myer |
| 4,776,353 A | 10/1988 | Lilja et al. |
| 4,793,365 A | 12/1988 | Sensabaugh, Jr. et al. |
| 4,800,903 A | 1/1989 | Ray et al. |
| 4,819,665 A | 4/1989 | Roberts et al. |
| 4,821,749 A | 4/1989 | Toft et al. |
| 4,830,028 A | 5/1989 | Lawson et al. |
| 4,836,224 A | 6/1989 | Lawson et al. |
| 4,836,225 A | 6/1989 | Sudoh |
| 4,848,374 A | 7/1989 | Chard et al. |
| 4,848,376 A | 7/1989 | Lilja et al. |
| 4,874,000 A | 10/1989 | Tamol et al. |
| 4,880,018 A | 11/1989 | Graves, Jr. et al. |
| 4,887,619 A | 12/1989 | Burcham, Jr. et al. |
| 4,907,606 A | 3/1990 | Lilja et al. |
| 4,913,168 A | 4/1990 | Potter et al. |
| 4,917,119 A | 4/1990 | Potter et al. |
| 4,917,128 A | 4/1990 | Clearman et al. |
| 4,922,901 A | 5/1990 | Brooks et al. |
| 4,924,888 A | 5/1990 | Perfetti et al. |
| 4,928,714 A | 5/1990 | Shannon |
| 4,938,236 A | 7/1990 | Banerjee et al. |
| 4,941,483 A | 7/1990 | Ridings et al. |
| 4,941,484 A | 7/1990 | Clapp et al. |
| 4,945,931 A | 8/1990 | Gori |
| 4,947,874 A | 8/1990 | Brooks et al. |
| 4,947,875 A | 8/1990 | Brooks et al. |
| 4,972,854 A | 11/1990 | Kiernan et al. |
| 4,972,855 A | 11/1990 | Kuriyama et al. |
| 4,986,286 A | 1/1991 | Roberts et al. |
| 4,987,906 A | 1/1991 | Young et al. |
| 5,005,593 A | 4/1991 | Fagg |
| 5,019,122 A | 5/1991 | Clearman et al. |
| 5,022,416 A | 6/1991 | Watson |
| 5,042,510 A | 8/1991 | Curtiss et al. |
| 5,052,413 A | 10/1991 | Baker et al. |
| 5,056,537 A | 10/1991 | Brown et al. |
| 5,060,669 A | 10/1991 | White et al. |
| 5,060,671 A | 10/1991 | Counts et al. |
| 5,065,775 A | 11/1991 | Fagg |
| 5,072,744 A | 12/1991 | Luke et al. |
| 5,074,319 A | 12/1991 | White et al. |
| 5,076,296 A | 12/1991 | Nystrom et al. |
| 5,093,894 A | 3/1992 | Deevi et al. |
| 5,095,921 A | 3/1992 | Losee et al. |
| 5,097,850 A | 3/1992 | Braunshteyn et al. |
| 5,099,862 A | 3/1992 | White et al. |
| 5,099,864 A | 3/1992 | Young et al. |
| 5,101,839 A | 4/1992 | Jakob et al. |
| 5,103,842 A | 4/1992 | Strang et al. |
| 5,121,757 A | 6/1992 | White et al. |
| 5,129,409 A | 7/1992 | White et al. |
| 5,131,415 A | 7/1992 | Munoz et al. |
| 5,143,097 A | 9/1992 | Sohn et al. |
| 5,144,962 A | 9/1992 | Counts et al. |
| 5,146,934 A | 9/1992 | Deevi et al. |
| 5,159,940 A | 11/1992 | Hayward et al. |
| 5,159,942 A | 11/1992 | Brinkley et al. |
| 5,179,966 A | 1/1993 | Losee et al. |
| 5,211,684 A | 5/1993 | Shannon et al. |
| 5,220,930 A | 6/1993 | Gentry |
| 5,224,498 A | 7/1993 | Deevi et al. |
| 5,228,460 A | 7/1993 | Sprinkel, Jr. et al. |
| 5,230,354 A | 7/1993 | Smith et al. |
| 5,235,992 A | 8/1993 | Sensabaugh |
| 5,243,999 A | 9/1993 | Smith |
| 5,246,018 A | 9/1993 | Deevi et al. |
| 5,249,586 A | 10/1993 | Morgan et al. |
| 5,261,424 A | 11/1993 | Sprinkel, Jr. |
| 5,269,327 A | 12/1993 | Counts et al. |
| 5,285,798 A | 2/1994 | Banerjee et al. |
| 5,293,883 A | 3/1994 | Edwards |
| 5,301,694 A | 4/1994 | Raymond |
| 5,303,720 A | 4/1994 | Banerjee et al. |
| 5,318,050 A | 6/1994 | Gonzalez-Parra et al. |
| 5,322,075 A | 6/1994 | Deevi et al. |
| 5,322,076 A | 6/1994 | Brinkley et al. |
| 5,339,838 A | 8/1994 | Young et al. |
| 5,345,951 A | 9/1994 | Serrano et al. |
| 5,353,813 A | 10/1994 | Deevi et al. |
| 5,357,984 A | 10/1994 | Farrier et al. |
| 5,360,023 A | 11/1994 | Blakley et al. |
| 5,369,723 A | 11/1994 | Counts et al. |
| 5,372,148 A | 12/1994 | McCafferty et al. |
| 5,377,698 A | 1/1995 | Litzinger et al. |
| 5,388,574 A | 2/1995 | Ingebrethsen et al. |
| 5,388,594 A | 2/1995 | Counts et al. |
| 5,408,574 A | 4/1995 | Deevi et al. |
| 5,435,325 A | 7/1995 | Clapp et al. |
| 5,445,169 A | 8/1995 | Brinkley et al. |
| 5,468,266 A | 11/1995 | Bensalem et al. |

(56) References Cited

U.S. PATENT DOCUMENTS

| | | |
|---|---|---|
| 5,468,936 A | 11/1995 | Deevi et al. |
| 5,479,948 A | 1/1996 | Counts et al. |
| 5,498,850 A | 3/1996 | Das |
| 5,498,855 A | 3/1996 | Deevi et al. |
| 5,499,636 A | 3/1996 | Baggett, Jr. et al. |
| 5,501,237 A | 3/1996 | Young et al. |
| 5,505,214 A | 4/1996 | Collins et al. |
| 5,515,842 A | 5/1996 | Ramseyer et al. |
| 5,530,225 A | 6/1996 | Hajaligol |
| 5,551,450 A | 9/1996 | Hemsley |
| 5,551,451 A | 9/1996 | Riggs et al. |
| 5,564,442 A | 10/1996 | MacDonald et al. |
| 5,573,692 A | 11/1996 | Das et al. |
| 5,591,368 A | 1/1997 | Fleischhauer et al. |
| 5,593,792 A | 1/1997 | Farrier et al. |
| 5,595,577 A | 1/1997 | Bensalem et al. |
| 5,596,706 A | 1/1997 | Shimazaki et al. |
| 5,611,360 A | 3/1997 | Tang |
| 5,613,504 A | 3/1997 | Collins et al. |
| 5,613,505 A | 3/1997 | Campbell et al. |
| 5,649,552 A | 7/1997 | Cho et al. |
| 5,649,554 A | 7/1997 | Sprinkel et al. |
| 5,659,656 A | 8/1997 | Das |
| 5,665,262 A | 9/1997 | Hajaligol et al. |
| 5,666,976 A | 9/1997 | Adams et al. |
| 5,666,977 A | 9/1997 | Higgins et al. |
| 5,666,978 A | 9/1997 | Counts et al. |
| 5,687,746 A | 11/1997 | Rose et al. |
| 5,692,525 A | 12/1997 | Counts et al. |
| 5,692,526 A | 12/1997 | Adams et al. |
| 5,708,258 A | 1/1998 | Counts et al. |
| 5,711,320 A | 1/1998 | Martin |
| 5,726,421 A | 3/1998 | Fleischhauer et al. |
| 5,727,571 A | 3/1998 | Meiring et al. |
| 5,730,158 A | 3/1998 | Collins et al. |
| 5,750,964 A | 5/1998 | Counts et al. |
| 5,799,663 A | 9/1998 | Gross et al. |
| 5,816,263 A | 10/1998 | Counts et al. |
| 5,819,756 A | 10/1998 | Mielordt |
| 5,829,453 A | 11/1998 | White et al. |
| 5,865,185 A | 2/1999 | Collins et al. |
| 5,865,186 A | 2/1999 | Volsey, II |
| 5,878,752 A | 3/1999 | Adams et al. |
| 5,880,439 A | 3/1999 | Deevi et al. |
| 5,894,841 A | 4/1999 | Voges |
| 5,915,387 A | 7/1999 | Baggett, Jr. et al. |
| 5,934,289 A | 8/1999 | Watkins et al. |
| 5,954,979 A | 9/1999 | Counts et al. |
| 5,967,148 A | 10/1999 | Harris et al. |
| 6,026,820 A | 2/2000 | Baggett, Jr. et al. |
| 6,033,623 A | 3/2000 | Deevi et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,116,247 A | 9/2000 | Banyasz et al. |
| 6,119,700 A | 9/2000 | Fleischhauer et al. |
| 6,125,853 A | 10/2000 | Susa et al. |
| 6,125,855 A | 10/2000 | Nevett et al. |
| 6,125,866 A | 10/2000 | Nichols et al. |
| 6,155,268 A | 12/2000 | Takeuchi |
| 6,164,287 A | 12/2000 | White |
| 6,182,670 B1 | 2/2001 | White |
| 6,196,218 B1 | 3/2001 | Voges |
| 6,196,219 B1 | 3/2001 | Hess et al. |
| 6,216,706 B1 | 4/2001 | Kumar et al. |
| 6,289,898 B1 | 9/2001 | Fournier et al. |
| 6,328,032 B1 | 12/2001 | Virtanen |
| 6,349,728 B1 | 2/2002 | Pham |
| 6,357,671 B1 | 3/2002 | Cewers |
| 6,418,938 B1 | 7/2002 | Fleischhauer et al. |
| 6,446,426 B1 | 9/2002 | Sweeney et al. |
| 6,532,965 B1 | 3/2003 | Abhulimen et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,701,936 B2 | 3/2004 | Shafer et al. |
| 6,715,494 B1 | 4/2004 | McCoy |
| 6,730,832 B1 | 5/2004 | Dominguez et al. |
| 6,772,756 B2 | 8/2004 | Shayan |
| 6,803,545 B2 | 10/2004 | Blake et al. |
| 6,803,550 B2 | 10/2004 | Sharpe et al. |
| 6,810,883 B2 | 11/2004 | Felter et al. |
| 6,854,461 B2 | 2/2005 | Nichols |
| 6,854,470 B1 | 2/2005 | Pu |
| 6,994,096 B2 | 2/2006 | Rostami et al. |
| 7,011,096 B2 | 3/2006 | Li et al. |
| 7,017,585 B2 | 3/2006 | Li et al. |
| 7,025,066 B2 | 4/2006 | Lawson et al. |
| 7,040,314 B2 | 5/2006 | Nguyen et al. |
| 7,117,867 B2 | 10/2006 | Cox et al. |
| 7,163,015 B2 | 1/2007 | Moffitt |
| 7,173,222 B2 | 2/2007 | Cox et al. |
| 7,185,659 B2 | 3/2007 | Sharpe et al. |
| 7,234,470 B2 | 6/2007 | Yang |
| 7,290,549 B2 | 11/2007 | Banerjee et al. |
| 7,293,565 B2 | 11/2007 | Griffin et al. |
| 7,392,809 B2 | 7/2008 | Larson et al. |
| 7,513,253 B2 | 4/2009 | Kobayashi et al. |
| 7,647,932 B2 | 1/2010 | Cantrell et al. |
| 7,690,385 B2 | 4/2010 | Moffitt |
| 7,692,123 B2 | 4/2010 | Baba et al. |
| 7,726,320 B2 | 6/2010 | Robinson et al. |
| 7,775,459 B2 | 8/2010 | Martens, III et al. |
| 7,810,505 B2 | 10/2010 | Yang |
| 7,832,410 B2 | 11/2010 | Hon |
| 7,845,359 B2 | 12/2010 | Montaser |
| 7,878,209 B2 | 2/2011 | Newbery et al. |
| 7,896,006 B2 | 3/2011 | Hamano et al. |
| 8,066,010 B2 | 11/2011 | Newbery et al. |
| 8,079,371 B2 | 12/2011 | Robinson et al. |
| 8,127,772 B2 | 3/2012 | Montaser |
| 8,156,944 B2 | 4/2012 | Han |
| 8,314,591 B2 | 11/2012 | Terry et al. |
| 8,365,742 B2 | 2/2013 | Hon |
| 8,375,957 B2 | 2/2013 | Hon |
| 8,393,331 B2 | 3/2013 | Hon |
| 8,402,976 B2 | 3/2013 | Fernando et al. |
| D685,522 S | 7/2013 | Potter |
| 8,499,766 B1 | 8/2013 | Newton |
| 8,528,569 B1 | 9/2013 | Newton |
| 8,550,069 B2 | 10/2013 | Alelov |
| 8,863,753 B2 | 10/2014 | Li |
| 8,881,737 B2 | 11/2014 | Collett |
| 8,910,639 B2 | 12/2014 | Chang |
| 8,910,640 B2 | 12/2014 | Sears |
| 9,132,248 B2 | 9/2015 | Qiu |
| 9,204,670 B2 | 12/2015 | Liu |
| 9,210,738 B2 | 12/2015 | Ward |
| 9,220,302 B2 | 12/2015 | DePiano |
| 9,277,770 B2 | 3/2016 | DePiano |
| 9,423,152 B2 | 8/2016 | Ampolini |
| 9,484,155 B2 | 11/2016 | Peckerar et al. |
| 9,491,974 B2 | 11/2016 | DePaino |
| 2002/0146242 A1 | 10/2002 | Vieira |
| 2003/0131859 A1 | 7/2003 | Li et al. |
| 2003/0226837 A1 | 12/2003 | Blake et al. |
| 2004/0020500 A1 | 2/2004 | Wrenn et al. |
| 2004/0118401 A1 | 6/2004 | Smith et al. |
| 2004/0129280 A1 | 7/2004 | Woodson et al. |
| 2004/0149296 A1 | 8/2004 | Rostami et al. |
| 2004/0200488 A1 | 10/2004 | Felter et al. |
| 2004/0226568 A1 | 11/2004 | Takeuchi et al. |
| 2004/0255965 A1 | 12/2004 | Perfetti et al. |
| 2005/0016549 A1 | 1/2005 | Banerjee et al. |
| 2005/0016550 A1 | 1/2005 | Katase |
| 2005/0066986 A1 | 3/2005 | Nestor et al. |
| 2005/0172976 A1 | 8/2005 | Newman et al. |
| 2005/0274390 A1 | 12/2005 | Banerjee et al. |
| 2006/0016453 A1 | 1/2006 | Kim |
| 2006/0070633 A1 | 4/2006 | Rostami et al. |
| 2006/0162733 A1 | 7/2006 | McGrath et al. |
| 2006/0185687 A1 | 8/2006 | Hearn et al. |

(56) References Cited

U.S. PATENT DOCUMENTS

| | | |
|---|---|---|
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2007/0262182 A1 | 11/2007 | De Groote et al. |
| 2007/0283972 A1 | 12/2007 | Monsees et al. |
| 2008/0085103 A1 | 4/2008 | Beland et al. |
| 2008/0092912 A1 | 4/2008 | Robinson et al. |
| 2008/0149118 A1 | 6/2008 | Oglesby et al. |
| 2008/0245377 A1 | 10/2008 | Marshall et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0065010 A1 | 3/2009 | Shands |
| 2009/0095311 A1 | 4/2009 | Hon |
| 2009/0095312 A1 | 4/2009 | Heibrich et al. |
| 2009/0126745 A1 | 5/2009 | Hon |
| 2009/0145503 A1 | 6/2009 | Green et al. |
| 2009/0188490 A1 | 7/2009 | Hon |
| 2009/0230117 A1 | 9/2009 | Fernando et al. |
| 2009/0260641 A1 | 10/2009 | Monsees et al. |
| 2009/0260642 A1 | 10/2009 | Monsees et al. |
| 2009/0272379 A1 | 11/2009 | Thorens et al. |
| 2009/0283103 A1 | 11/2009 | Nielsen et al. |
| 2009/0293892 A1 | 12/2009 | Williams et al. |
| 2009/0302019 A1 | 12/2009 | Selenski et al. |
| 2009/0320863 A1 | 12/2009 | Fernando et al. |
| 2009/0324206 A1 | 12/2009 | Young et al. |
| 2010/0006113 A1 | 1/2010 | Urtsev et al. |
| 2010/0024834 A1 | 2/2010 | Oglesby et al. |
| 2010/0043809 A1 | 2/2010 | Magnon |
| 2010/0059070 A1 | 3/2010 | Potter et al. |
| 2010/0059073 A1 | 3/2010 | Hoffmann et al. |
| 2010/0065075 A1 | 3/2010 | Banerjee et al. |
| 2010/0083959 A1 | 4/2010 | Siller |
| 2010/0163063 A1 | 7/2010 | Fernando et al. |
| 2010/0200006 A1 | 8/2010 | Robinson et al. |
| 2010/0229881 A1 | 9/2010 | Hearn |
| 2010/0242974 A1 | 9/2010 | Pan |
| 2010/0242976 A1 | 9/2010 | Katayama et al. |
| 2010/0258139 A1 | 10/2010 | Onishi et al. |
| 2010/0300467 A1 | 12/2010 | Kuistila et al. |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0073121 A1 | 3/2011 | Levin et al. |
| 2011/0088707 A1 | 4/2011 | Hajaligol |
| 2011/0094523 A1 | 4/2011 | Thorens et al. |
| 2011/0120480 A1 | 5/2011 | Gedevanishvili et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0162663 A1 | 7/2011 | Bryman |
| 2011/0168194 A1 | 7/2011 | Hon |
| 2011/0180082 A1 | 7/2011 | Banerjee et al. |
| 2011/0226236 A1 | 9/2011 | Buchberger |
| 2011/0265806 A1 | 11/2011 | Alarcon et al. |
| 2011/0297166 A1 | 12/2011 | Takeuchi et al. |
| 2011/0304282 A1 | 12/2011 | Li et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0180803 A1 | 7/2012 | Beloni |
| 2012/0199663 A1 | 8/2012 | Qiu |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0285475 A1 | 11/2012 | Liu |
| 2012/0318283 A1 | 12/2012 | Watanabe et al. |
| 2012/0318882 A1 | 12/2012 | Abehasera |
| 2013/0008457 A1 | 1/2013 | Zheng et al. |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0220315 A1 | 8/2013 | Conley et al. |
| 2013/0255675 A1 | 10/2013 | Liu |
| 2013/0255702 A1 | 10/2013 | Griffith, Jr. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian |
| 2014/0034071 A1 | 2/2014 | Levitz et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0253144 A1 | 9/2014 | Novak, III |
| 2014/0261486 A1 | 9/2014 | Potter |
| 2014/0261487 A1 | 9/2014 | Chapman |
| 2014/0353856 A1 | 12/2014 | Dubief |

FOREIGN PATENT DOCUMENTS

| | | |
|---|---|---|
| CA | 2 752 255 | 8/2010 |
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 202335348 | 7/2012 |
| DE | 10 2006 004 484 | 8/2007 |
| DE | 102006041042 | 3/2008 |
| DE | 20 2009 010 400 | 11/2009 |
| EA | 019736 | 5/2014 |
| EP | 0 295 122 | 12/1988 |
| EP | 0 430 566 | 6/1991 |
| EP | 0 845 220 | 6/1998 |
| EP | 0 706 352 | 3/2002 |
| EP | 1 618 803 | 1/2006 |
| EP | 2 022 349 | 2/2009 |
| EP | 2 316 286 | 5/2011 |
| EP | 1 996 037 | 4/2012 |
| EP | 2 468 116 | 6/2012 |
| EP | 1 993 388 | 8/2012 |
| EP | 2 870 887 | 5/2015 |
| GB | 653598 | 5/1951 |
| GB | 1444461 | 7/1976 |
| GB | 2469850 | 11/2010 |
| JP | S 62-110689 | 7/1987 |
| JP | 2004/011693 | 1/2004 |
| RU | 89927 | 12/2009 |
| WO | WO 1986/02528 | 5/1986 |
| WO | WO 1997/48293 | 12/1997 |
| WO | WO 98/57556 | 12/1998 |
| WO | WO 02/37990 | 5/2002 |
| WO | WO 2004/043175 | 5/2004 |
| WO | WO 2005/099494 | 10/2005 |
| WO | WO 2006/103792 | 10/2006 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/045671 | 4/2010 |
| WO | WO 2010/073122 | 7/2010 |
| WO | WO 2010/091593 | 8/2010 |
| WO | WO 2010/118644 | 10/2010 |
| WO | WO 2010/140841 | 12/2010 |
| WO | WO 2010/140937 | 12/2010 |
| WO | WO 2011/010334 | 1/2011 |
| WO | WO 2011/081558 | 7/2011 |
| WO | WO 2011/147687 | 12/2011 |
| WO | WO 2011/147714 | 12/2011 |

(56) References Cited

FOREIGN PATENT DOCUMENTS

| WO | WO 2012/058941 | 5/2012 |
| WO | WO 2012/072762 | 6/2012 |
| WO | WO 2012/100523 | 8/2012 |
| WO | WO 2012/170424 | 12/2012 |
| WO | WO 2013/089551 | 6/2013 |
| WO | WO 2013/116567 | 8/2013 |

OTHER PUBLICATIONS

Notices of Opposition filed in corresponding European Application No. 14716487.5, Patent No. 2967149, on May 15, 2019.

CARTRIDGE AND CONTROL BODY OF AN AEROSOL DELIVERY DEVICE INCLUDING ANTI-ROTATION MECHANISM AND RELATED METHOD

CROSS-REFERENCE TO RELATED APPLICATIONS

This application is a divisional of U.S. patent application Ser. No. 15/434,963, filed Feb. 16, 2017, which is a continuation of U.S. patent application Ser. No. 13/840,264, filed Mar. 15, 2013 (now issued as U.S. Pat. No. 9,609,893 on Apr. 4, 2017), which applications are hereby incorporated by reference in their entireties in this application.

FIELD OF THE DISCLOSURE

The present disclosure relates to a cartridge and a control body of an aerosol delivery device such as a smoking article, and more particularly to a cartridge and a control body of an aerosol delivery device such as a smoking article including an anti-rotation mechanism. The smoking article may be configured to heat an aerosol precursor, which may be made or derived from tobacco or otherwise incorporate tobacco, to form an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. patent application Ser. No. 13/432,406, filed Mar. 28, 2012, U.S. patent application Ser. No. 13/536,438, filed Jun. 28, 2012, U.S. patent application Ser. No. 13/602,871, filed Sep. 4, 2012, and U.S. patent application Ser. No. 13/647,000, filed Oct. 8, 2012, which are incorporated herein by reference.

Certain tobacco products that have employed electrical energy to produce heat for smoke or aerosol formation, and in particular, certain products that have been referred to as electronic cigarette products, have been commercially available throughout the world. Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; COHITA™, COLIBRI™, ELITE CLASSIC™, MAGNUM™, PHANTOM™ and SENSE™ by Epuffer® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; GREEN SMOKE® by Green Smoke Inc. USA; GREENARETTE™ by Greenarette LLC; HALLIGAN™, HENDU™, JET™, MAXXQ™, PINK™ and PITBULL™ by Smoke Stik®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC and VUSE® by R. J. Reynolds Vapor Company. Yet other electrically powered aerosol delivery devices, and in particular those devices that have been characterized as so-called electronic cigarettes, have been marketed under the tradenames BLU™; COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP® and SOUTH BEACH SMOKE™.

It would be desirable to provide an aerosol delivery device that employs heat produced by electrical energy to provide the sensations of cigarette, cigar, or pipe smoking, that does so without combusting tobacco to any significant degree, that does so without the need of a combustion heat source, and that does so without necessarily delivering considerable quantities of incomplete combustion and pyrolysis products. Further, it would be desirable to provide an aerosol delivery device that employs convenient releasable engagement between a control body and a cartridge thereof.

BRIEF SUMMARY OF THE DISCLOSURE

In one aspect a cartridge for an aerosol delivery device is provided. The cartridge may include a reservoir substrate configured to hold an aerosol precursor composition, an atomizer configured to atomize the aerosol precursor, and a base extending between a body end oriented toward the reservoir substrate and the atomizer and a connector end configured to releasably engage a control body. The base may include an anti-rotation mechanism at the connector end configured to prevent rotation of the cartridge relative to the control body when engaged therewith.

In some embodiments the anti-rotation mechanism may include a plurality of protrusions and a plurality of recesses alternatingly disposed about an inner periphery of the base. A width of each of the protrusions may increase from the connector end toward the body end and a width of each of the recesses may decrease from the connector end toward the body end. The cartridge may additionally include a plurality of ribs extending from the inner periphery of the base at the recesses. A radial dimension of the inner periphery of the base may decrease from the connector end toward the body end. The base may further include a groove extending at least partially around the inner periphery thereof.

In an additional aspect a control body for an aerosol delivery device is provided. The control body may include a control component, an electrical power source, and a coupler extending between a body end oriented toward the control component and the electrical power source and a connector end configured to releasably engage a cartridge. The coupler may include an anti-rotation mechanism at the connector end configured to prevent rotation of the control body relative to the cartridge when engaged therewith.

In some embodiments the anti-rotation mechanism may include a plurality of protrusions and a plurality of recesses alternatingly disposed about an outer periphery of the coupler. A width of each of the protrusions may increase from the connector end toward the body end, and a width of each of the recesses may decrease from the connector end toward the body end. A radial dimension of the outer periphery of the coupler may increase from the connector end toward the body end. The coupler may additionally include a circumferential protrusion extending at least partially around the outer periphery thereof.

In a further aspect an aerosol delivery device is provided. The aerosol delivery device may include a control body. The control body may include a control component, an electrical power source, a coupler extending between a body end oriented toward the control component and the electrical power source and a connector end comprising an anti-rotation mechanism. The aerosol delivery device may additionally include a cartridge. The cartridge may include a reservoir substrate configured to hold an aerosol precursor composition, an atomizer configured to atomize the aerosol precursor, and a base extending between a body end oriented toward the reservoir substrate and the atomizer and a connector end configured to releasably engage the control body. The connector end of the base may include an anti-rotation mechanism configured to engage the anti-rotation mechanism of the coupler of the control body to prevent rotation of the cartridge relative to the control body when engaged therewith.

In some embodiments the anti-rotation mechanism of the base may include a plurality of protrusions and a plurality of recesses alternatingly disposed about an inner periphery thereof and the anti-rotation mechanism of the coupler may include a plurality of protrusions and a plurality of recesses alternatingly disposed about an outer periphery thereof. A width of each of the protrusions of the base and the protrusions of the coupler may respectively increase from the connector end toward the body end and a width of each of the recesses of the base and the recesses of the coupler may respectively decrease from the connector end toward the body end. The base may further include a plurality of ribs extending from the inner periphery thereof at the recesses. A radial dimension of the inner periphery of the base may decrease from the connector end toward the body end and a radial dimension of the outer periphery of the coupler may increase from the connector end toward the body end. The base may further include a groove extending at least partially around the inner periphery thereof and the coupler may additionally include a circumferential protrusion extending at least partially around the outer periphery thereof.

In another aspect a method for forming an aerosol delivery device is provided. The method may include providing a control body and a coupler, which may respectively include some or all of the features described above. Further the method may include engaging the connector end of the base to the connector end of the coupler such that the cartridge releasably engages the control body and the anti-rotation mechanism of the control body engages the anti-rotation mechanism of the cartridge to substantially prevent rotation of the cartridge relative to the control body. In some embodiments engaging the connector end of the base to the connector end of the coupler may include engaging a plurality of protrusions and a plurality of recesses alternatingly disposed about an inner periphery of the base of the cartridge with a plurality of protrusions and a plurality of recesses alternatingly disposed about an outer periphery of the control body. In some embodiments engaging the connector end of the base to the connector end of the coupler may additionally include engaging a plurality of ribs extending from the inner periphery of the base at the recesses with the protrusions of the control body. Engaging the connector end of the base to the connector end of the coupler may further include engaging a circumferential protrusion extending at least partially around the outer periphery of the coupler with a groove extending at least partially around the inner periphery of the base.

BRIEF DESCRIPTION OF THE FIGURES

Having thus described the disclosure in the foregoing general terms, reference will now be made to the accompanying drawings, which are not necessarily drawn to scale, and wherein:

FIG. 1 illustrates a sectional view through an aerosol delivery device comprising a control body and a cartridge including an atomizer according to an example embodiment of the present disclosure;

FIG. 2 illustrates an exploded view of a control body of an aerosol delivery device according to an example embodiment of the present disclosure;

FIG. 3 illustrates the control body of FIG. 2 in a partially assembled configuration with an adhesive member and an outer tube removed for clarity purposes;

FIG. 4 illustrates the control body of FIG. 2 in a partially assembled configuration with outer tube removed for clarity purposes;

FIG. 5 illustrates the control body of FIG. 2 in an assembled configuration;

FIG. 6 illustrates a partially exploded view of an aerosol delivery device including the control body of FIG. 2 in the assembled configuration and a cartridge in an exploded configuration, the cartridge comprising a base shipping plug, a base, a control component terminal, an electronic control component, a flow tube, an atomizer, a reservoir substrate, an external shell, a label, a mouthpiece, and a mouthpiece shipping plug according to an example embodiment of the present disclosure;

FIG. 7 illustrates an enlarged exploded view of the base and the control component terminal of the cartridge of FIG. 6;

FIG. 8 illustrates an enlarged perspective view of the base and the control component terminal of FIG. 6 in an assembled configuration;

FIG. 9 illustrates an enlarged perspective view of the base, the control component terminal, the electronic control component, and heater terminals of the atomizer of FIG. 6 in an assembled configuration;

FIG. 10 illustrates an enlarged perspective view of the base, the atomizer, and the control component of FIG. 6 in an assembled configuration;

FIG. 11 illustrates an opposing perspective view of the assembly of FIG. 10;

FIG. 12 illustrates an enlarged perspective view of the base, the atomizer, the flow tube, and the reservoir substrate of FIG. 6 in an assembled configuration;

FIG. 13 illustrates a perspective view of the base and the external shell of FIG. 6 in an assembled configuration;

FIG. 14 illustrates a perspective view of the cartridge of FIG. 6 in an assembled configuration;

FIG. 15 illustrates a first partial perspective view of the cartridge of FIG. 6 and a coupler for a control body according to an example embodiment of the present disclosure;

DETAILED DESCRIPTION OF PREFERRED EMBODIMENTS

Figure 1:
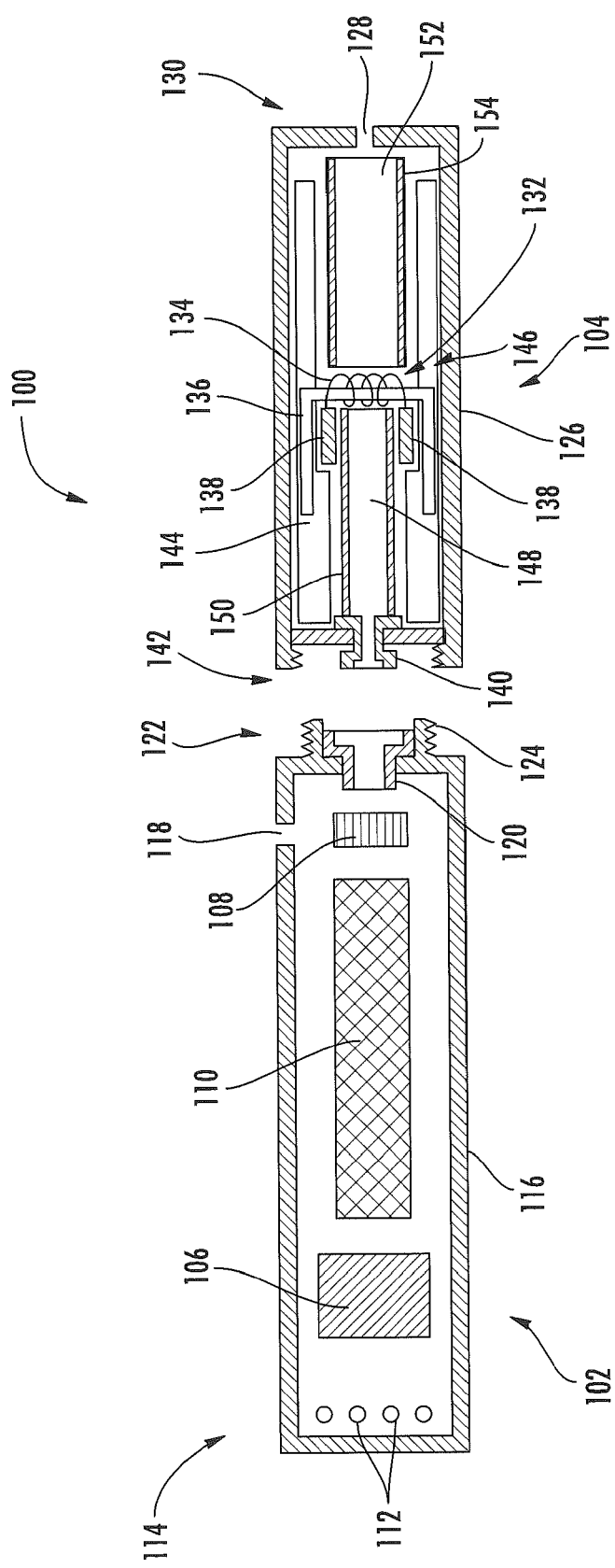

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure provides descriptions of aerosol delivery devices that use electrical energy to heat a material (preferably without combusting the material to any significant degree) to form an inhalable substance; such articles most preferably being sufficiently compact to be considered "hand-held" devices. In certain highly preferred embodiments, the aerosol delivery devices can be characterized as smoking articles. As used herein, the term "smoking article" is intended to mean an article or device that provides some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. As used herein, the term "smoking article" does not necessarily mean that, in operation, the article or device produces smoke in the sense of the aerosol resulting from by-products of combustion or pyrolysis of tobacco, but rather, that the article or device yields vapors (including vapors within aerosols that can be considered to be visible aerosols that might be considered to be described as smoke-like) resulting from volatilization or vaporization of certain components of the article or device. In highly preferred embodiments, articles or devices characterized as smoking articles incorporate tobacco and/or components derived from tobacco.

Articles or devices of the present disclosure also can be characterized as being vapor-producing articles, aerosol delivery articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, smoking articles of the present disclosure may be subjected to many of the physical actions employed by an individual in using a traditional type of smoking article (e.g., a cigarette, cigar or pipe that is employed by lighting and inhaling tobacco). For example, the user of a smoking article of the present disclosure can hold that article much like a traditional type of smoking article, draw on one end of that article for inhalation of aerosol produced by that article, take puffs at selected intervals of time, etc.

Smoking articles of the present disclosure generally include a number of components provided within an outer shell or body. The overall design of the outer shell or body can vary, and the format or configuration of the outer body that can define the overall size and shape of the smoking article can vary. Typically, an elongated body resembling the shape of a cigarette or cigar can be a formed from a single, unitary shell; or the elongated body can be formed of two or more separable pieces. For example, a smoking article can comprise an elongated shell or body that can be substantially tubular in shape and, as such, resemble the shape of a conventional cigarette or cigar. In one embodiment, all of the components of the smoking article are contained within one outer body or shell. Alternatively, a smoking article can comprise two or more shells that are joined and are separable. For example, a smoking article can possess at one end a control body comprising a shell containing one or more reusable components (e.g., a rechargeable battery and various electronics for controlling the operation of that article), and at the other end and removably attached thereto a shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various smoking article designs and component arrangements can be appreciated upon consideration of the commercially available electronic smoking articles, such as those representative products listed in the background art section of the present disclosure.

Smoking articles of the present disclosure most preferably comprise some combination of a power source (i.e., an electrical power source), at least one control component (e.g., means for actuating, controlling, regulating and ceasing power for heat generation, such as by controlling electrical current flow the power source to other components of the article), a heater or heat generation component (e.g., an electrical resistance heating element or component commonly referred to as an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the smoking article for aerosol inhalation (e.g., a defined air flow path through the article such that aerosol generated can be withdrawn therefrom upon draw). Exemplary formulations for aerosol precursor materials that may be used according to the present disclosure are described in U.S. Pat. Pub. No. 2013/0008457 to Zheng et al., the disclosure of which is incorporated herein by reference in its entirety.

Alignment of the components within the article can vary. In specific embodiments, the aerosol precursor composition can be located near an end of the article (e.g., within a cartridge, which in certain circumstances can be replaceable and disposable), which may be is proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various smoking article components can be appreciated upon consideration of the commercially available electronic smoking articles, such as those representative products listed in the background art section of the present disclosure.

A smoking article incorporates a battery or other electrical power source to provide current flow sufficient to provide various functionalities to the article, such as resistive heating, powering of control systems, powering of indicators, and the like. The power source can take on various embodiments. Preferably, the power source is able to deliver sufficient power to rapidly heat the heating member to provide for aerosol formation and power the article through use for the desired duration of time. The power source preferably is sized to fit conveniently within the article so that the article can be easily handled; and additionally, a preferred power source is of a sufficiently light weight to not detract from a desirable smoking experience.

One example embodiment of a smoking article 100 is provided in FIG. 1. As seen in the cross-section illustrated therein, the smoking article 100 can comprise a control body 102 and a cartridge 104 that can be permanently or detachably aligned in a functioning relationship. Although a threaded engagement is illustrated in FIG. 1, it is understood that further means of engagement are encompassed, such as a press-fit engagement, interference fit, a magnetic engagement, or the like.

In specific embodiments, one or both of the control body 102 and the cartridge 104 may be referred to as being disposable or as being reusable. For example, the control body may have a replaceable battery or a rechargeable battery and thus may be combined with any type of recharging technology, including connection to a typical electrical outlet, connection to a car charger (i.e., cigarette lighter receptacle), and connection to a computer, such as through a universal serial bus (USB) cable.

In the exemplified embodiment, the control body 102 includes a control component 106, a flow sensor 108, and a battery 110, which can be variably aligned, and can include a plurality of indicators 112 at a distal end 114 of an external shell 116. The indicators 112 can be provided in varying numbers and can take on different shapes and can even be an opening in the body (such as for release of sound when such indicators are present).

An air intake 118 may be positioned in the external shell 116 of the control body 102. A coupler 120 also is included at the proximal attachment end 122 of the control body 102 and extends into a control body projection 124 to allow for ease of electrical connection with an atomizer or a component thereof, such as a resistive heating element (described below) when the cartridge 104 is attached to the control body.

The cartridge 104 includes an external shell 126 with a mouth opening 128 at a mouthend 130 thereof to allow passage of air and entrained vapor (i.e., the components of the aerosol precursor composition in an inhalable form) from the cartridge to a consumer during draw on the smoking article 100. The smoking article 100 may be substantially rod-like or substantially tubular shaped or substantially cylindrically shaped in some embodiments.

The cartridge 104 further includes an atomizer 132 comprising a resistive heating element 134 comprising a wire coil in the illustrated embodiment and a liquid transport element 136 comprising a wick in the illustrated embodiment and configured to transport a liquid. Various embodiments of materials configured to produce heat when electrical current is applied therethrough may be employed to form the wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum (Mo (Si,Al)$_2$), and ceramic (e.g., a positive temperature coefficient ceramic). Electrically conductive heater terminals 138 (e.g., positive and negative terminals) at the opposing ends of the heating element 134 are configured to direct current flow through the heating element and configured for attachment to the appropriate wiring or circuit (not illustrated) to form an electrical connection of the heating element with the battery 110 when the cartridge 104 is connected to the control body 102. Specifically, a plug 140 may be positioned at a distal attachment end 142 of the cartridge 104. When the cartridge 104 is connected to the control body 102, the plug 140 engages the coupler 120 to form an electrical connection such that current controllably flows from the battery 110, through the coupler and plug, and to the heating element 134. The external shell 126 of the cartridge 104 can continue across the distal attachment end 142 such that this end of the cartridge is substantially closed with the plug 140 protruding therefrom.

A reservoir may utilize a liquid transport element to transport an aerosol precursor composition to an aerosolization zone. One such example is shown in FIG. 1. As seen therein, the cartridge 104 includes a reservoir layer 144 comprising layers of nonwoven fibers formed into the shape of a tube encircling the interior of the external shell 126 of the cartridge, in this embodiment. An aerosol precursor composition is retained in the reservoir layer 144. Liquid components, for example, can be sorptively retained by the reservoir layer 144. The reservoir layer 144 is in fluid connection with a liquid transport element 136 (the wick in this embodiment). The liquid transport element 136 transports the aerosol precursor composition stored in the reservoir layer 144 via capillary action to an aerosolization zone 146 of the cartridge 104. As illustrated, the liquid transport element 136 is in direct contact with the heating element 134 that is in the form of a metal wire coil in this embodiment.

In use, when a user draws on the article 100, the heating element 134 is activated (e.g., such as via a puff sensor), and the components for the aerosol precursor composition are vaporized in the aerosolization zone 146. Drawing upon the mouthend 130 of the article 100 causes ambient air to enter the air intake 118 and pass through the central opening in the coupler 120 and the central opening in the plug 140. In the cartridge 104, the drawn air passes through an air passage 148 in an air passage tube 150 and combines with the formed vapor in the aerosolization zone 146 to form an aerosol. The aerosol is whisked away from the aerosolization zone 146, passes through an air passage 152 in an air passage tube 154, and out the mouth opening 128 in the mouthend 130 of the article 100.

It is understood that a smoking article that can be manufactured according to the present disclosure can encompass a variety of combinations of components useful in forming an electronic smoking article. Reference is made for example to the smoking articles disclosed in U.S. patent application Ser. No. 13/536,438, filed Jun. 28, 2012, U.S. patent application Ser. No. 13/432,406, filed Mar. 28, 2012, U.S. patent application Ser. No. 13/602,871, filed Sep. 4, 2012, the disclosures of which are incorporated herein by reference in their entirety. Further to the above, representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, a single-use cartridge for use with an electronic smoking article is disclosed in U.S. patent application Ser. No. 13/603,612, filed Sep. 5, 2012, which is incorporated herein by reference in its entirety.

The various components of a smoking article according to the present disclosure can be chosen from components described in the art and commercially available. Examples of batteries that can be used according to the disclosure are described in U.S. Pat. App. Pub. No. 2010/0028766, the disclosure of which is incorporated herein by reference in its entirety.

An exemplary mechanism that can provide puff-actuation capability includes a Model 163PC01D36 silicon sensor, manufactured by the MicroSwitch division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Further description of current regulating circuits and other control components, including microcontrollers that can be useful in the present smoking article, are provided in U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties.

The aerosol precursor, which may also be referred to as an aerosol precursor composition or a vapor precursor composition, can comprise one or more different components. For example, the aerosol precursor can include a polyhydric alcohol (e.g., glycerin, propylene glycol, or a mixture thereof). Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference.

Still further components can be utilized in the smoking article of the present disclosure. For example, U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. App. Pub. No. 2009/0320863 by Fernando et al. discloses computer interfacing means for smoking devices to facilitate charging and allow computer control of the device; U.S. Pat. App. Pub. No. 2010/0163063 by Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. No. 8,156,944 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon. A variety of the materials disclosed by the foregoing documents may be incorporated into the present devices in various embodiments, and all of the foregoing disclosures are incorporated herein by reference in their entireties.

Figure 2:
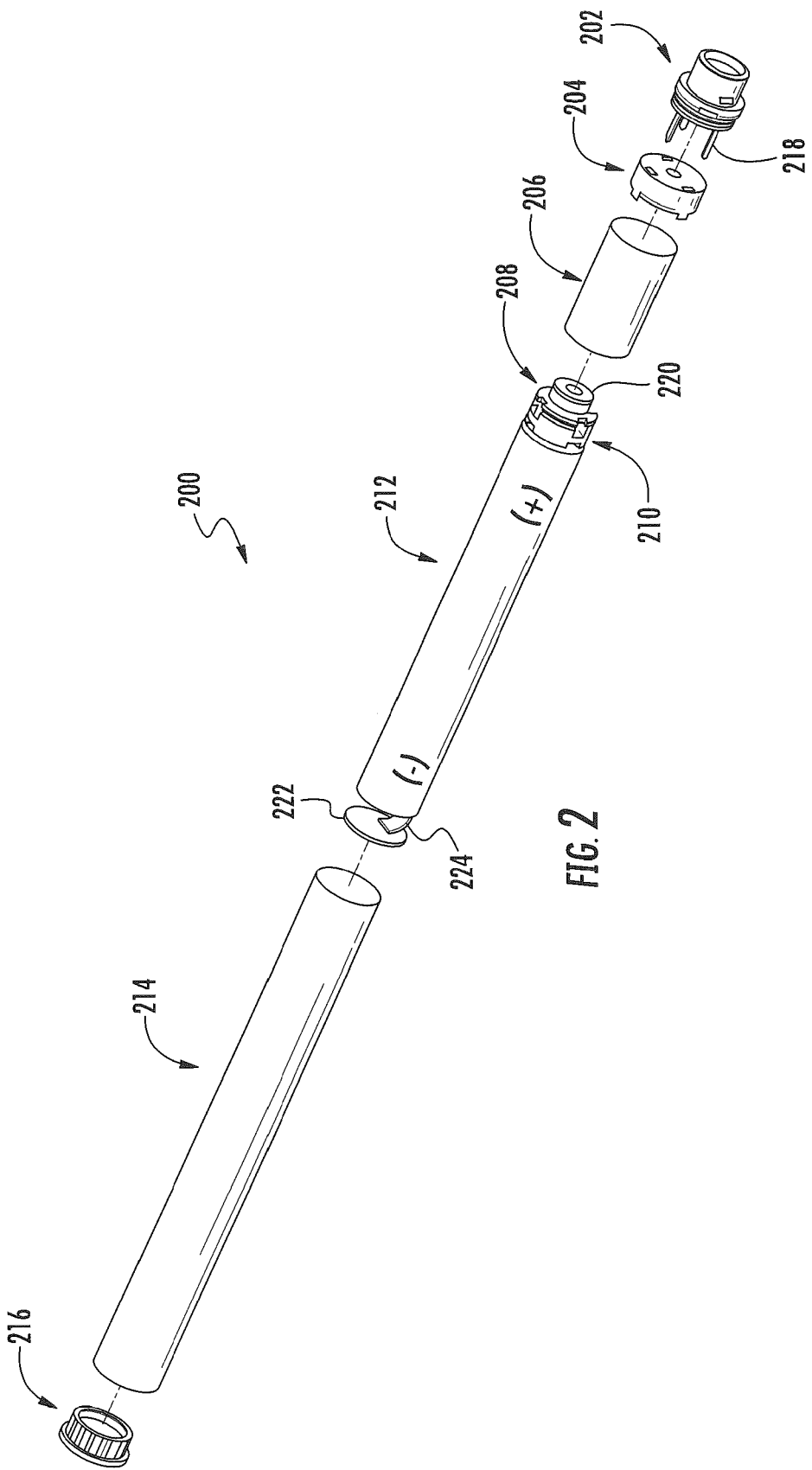

FIG. 2 illustrates an exploded view of a control body 200 for an aerosol delivery device according to an example embodiment of the present disclosure. The components of the control body 200 are described only briefly below due to the description of the control body illustrated in FIG. 1 being applicable to the components of the control body illustrated in FIG. 2. As illustrated, the control body 200 may comprise a coupler 202, a sealing member 204, an adhesive member 206 (e.g., KAPTON® tape), a flow sensor 220, a control component 208, a spacer 210, an electrical power source 212 (e.g., a battery), a circuit board with a light emitting diode (LED) component 222, a connector circuit 224, an outer tube 214, and an end cap 216.

The coupler 202 may include control body terminals 218 extending therefrom which may extend through the sealing member 204 and engage one or both of the control component 208 and the electrical power source 212. The control component 208 may be a printed circuit board including a microcontroller. The flow sensor 220 may be coupled to the control component 208 or may be a separate element. The LED component 222 can be in communication with the control component 208 through the connector circuit 224 and illuminate, for example, during a user drawing on a cartridge coupled to the coupler 202, as detected by the flow sensor 220. The end cap 216 may be adapted to make visible the LED illumination thereunder provided by the LED component 222.

Figure 3:
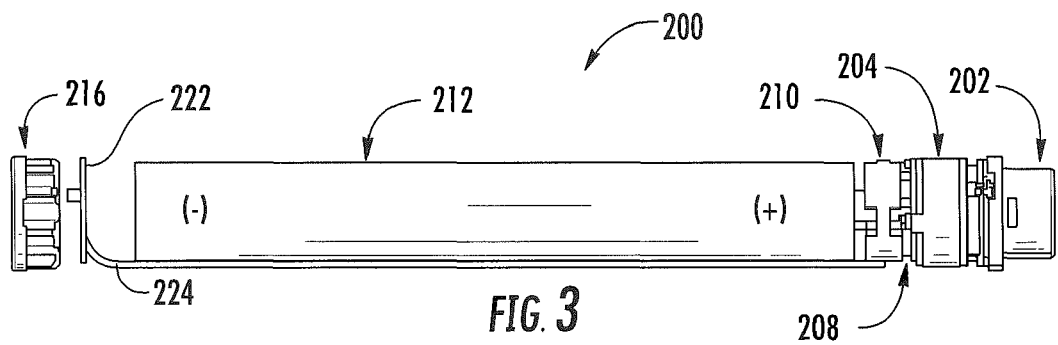
Figure 4:
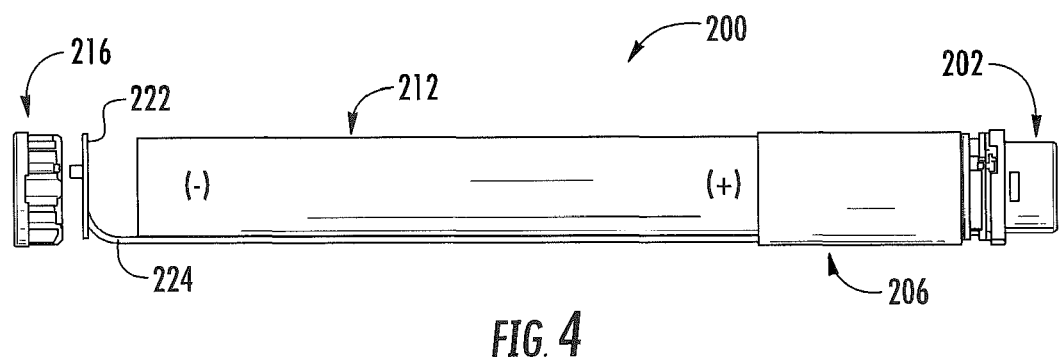
Figure 5:
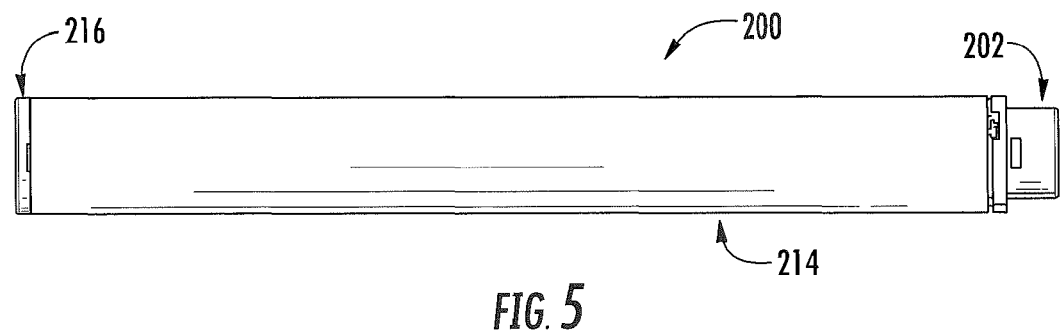

FIGS. 3-5 illustrate the control body 202 in various states of assembly. More particularly, FIG. 3 illustrates the control body 200 with the adhesive member 206 and the outer tube 214 removed for clarity purposes. FIG. 4 illustrates the control body 200 with the outer tube 214 removed for clarity purposes. FIG. 5 illustrates the control body in a fully-assembled configuration.

Figure 6:
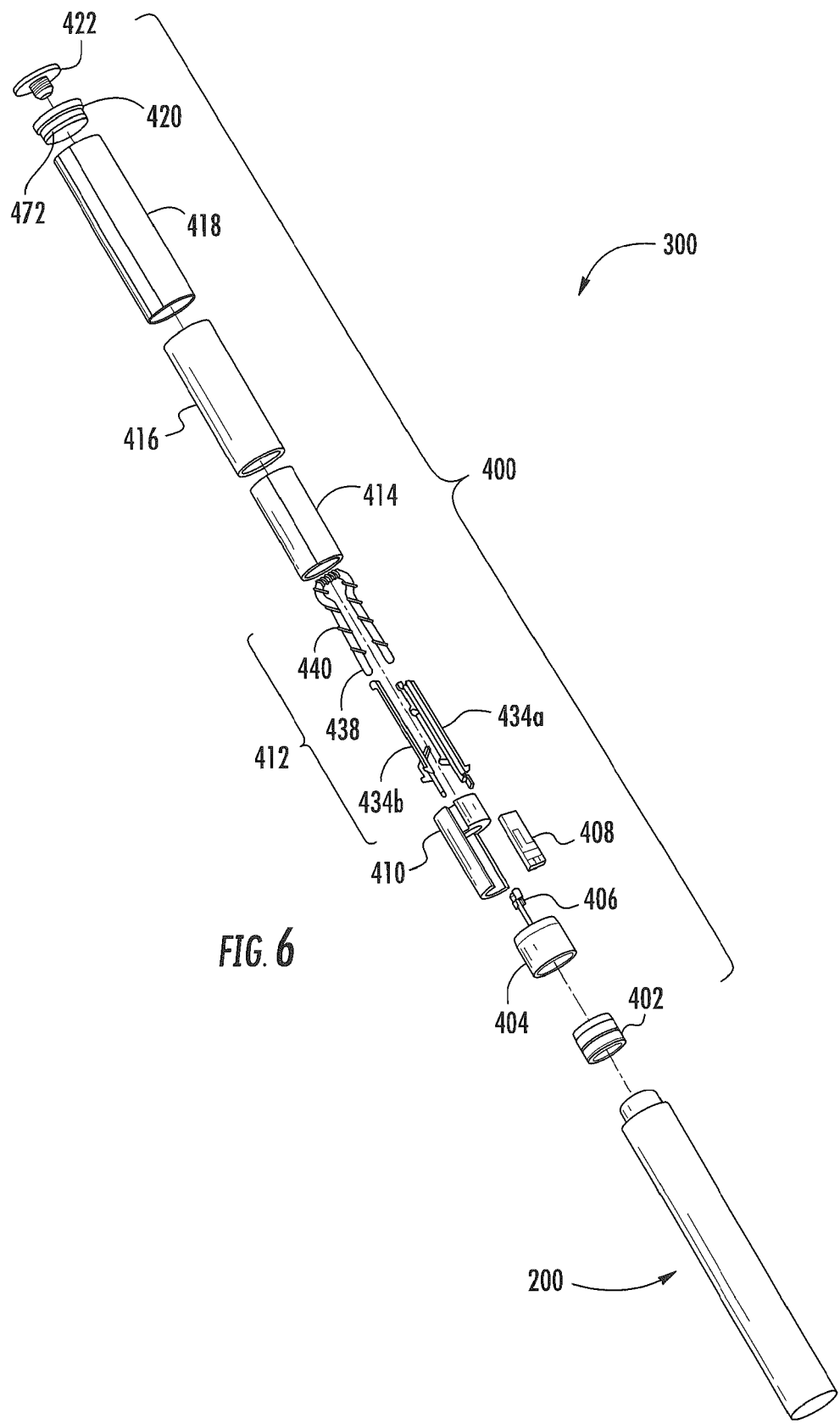

FIG. 6 illustrates a partially exploded view of an aerosol delivery device 300 including the control body 200 of FIGS. 2-5 in the assembled configuration and a cartridge 400 in an exploded configuration. As illustrated, the cartridge 400 may comprise a base shipping plug 402, a base 404, a control component terminal 406, an electronic control component 408, a flow tube 410, an atomizer 412, a reservoir substrate 414, an external shell 416, a label 418, a mouthpiece 420, and a mouthpiece shipping plug 422 according to an example embodiment of the present disclosure. Note that the various embodiments of components described above in the cited references and/or included in commercially available aerosol delivery devices may be employed in embodiments of the cartridges described herein. Note further that some of the portions of the cartridge 400 illustrated in FIG. 6 are optional. In this regard, by way of example, the cartridge 400 may not include the flow tube 410, the control component terminal 406, and/or the electronic control component 408 in some embodiments.

In one embodiment the electronic control component 408 may comprise a single-piece printed circuit board assembly.

The electronic control component 408 may include a ceramic substrate, which may comprise about 96% alumina ceramic in one embodiment. This material is inorganic, non-reactive, non-degrading, and non-porous. Use of such a ceramic material may be preferable in that it may define a robust, dimensionally-stable part without requiring a separate supporting structure. Further, such a ceramic material may allow for adhesion of a coating thereto. For example, a component side of the electronic control component 408 may comprise a chloro-substituted poly (para-xylylene) commercially available as Parylene C from Specialty Coating Systems, Inc., or any other coating or other sealant/barrier coating configured to protect components of the circuit board from liquid and moisture. The sealant/barrier coating may also provide the electronic control component 408 with a decreased coefficient of friction, which may facilitate an axial assembly process of the cartridge 400.

Figure 7:
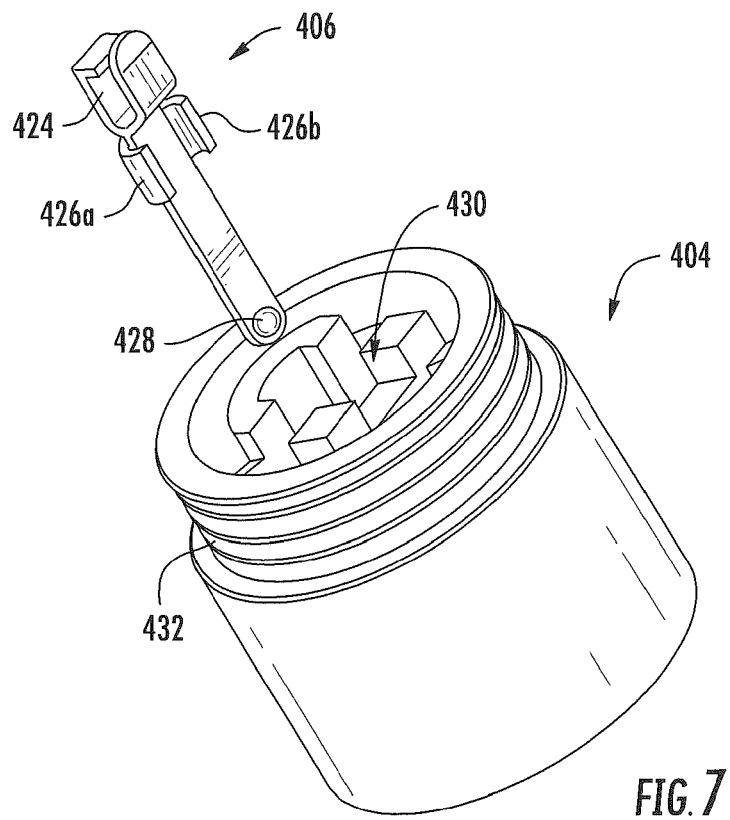

FIG. 7 illustrates an enlarged exploded view of the base 404 and the control component terminal 406. The control component terminal 406 may define a clip 424 configured to engage the electronic control component 408 and form an electrical connection therewith. Further, the control component terminal 406 may include one or more protrusions 426a, 426b configured to engage the base 404, for example via interference fit, such that the control component terminal 406 is retained in engagement therewith. An end 428 of the control component terminal 406 may be configured to engage a control body, so as to establish an electrical connection therewith.

Figure 8:
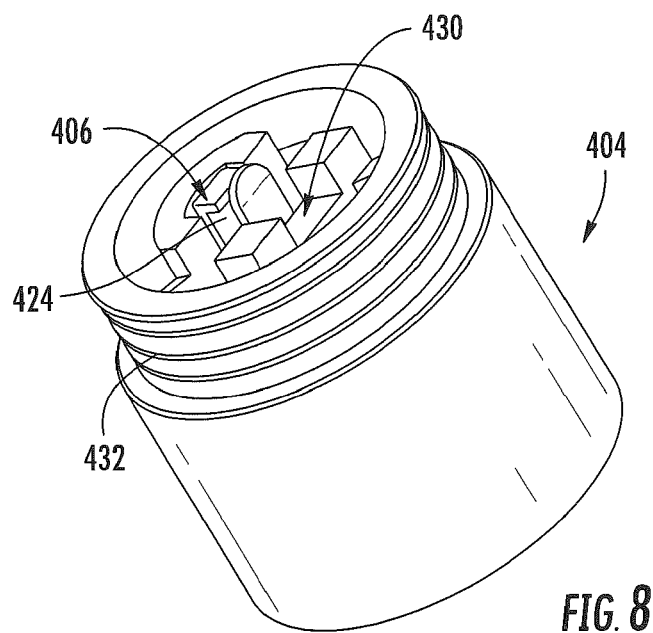

As illustrated, the base 404 may define a receptacle 430 configured to receive the control component terminal 406 therein. In this regard, as illustrated in FIG. 8, the control component terminal 406 may couple to the base 404. For example, the control component terminal 406 may be retained in the receptacle 430 of the base 404 via interference fit, for example due to contact between the protrusions 426a, 426b and the base. The control component terminal 406 may extend through the base 404 to a position at which it may form an electrical connection with the control body 200 to which the cartridge 400 connects. Further, the base 404 may define threads or protrusions 432 configured to engage the external shell 416.

Figure 9:
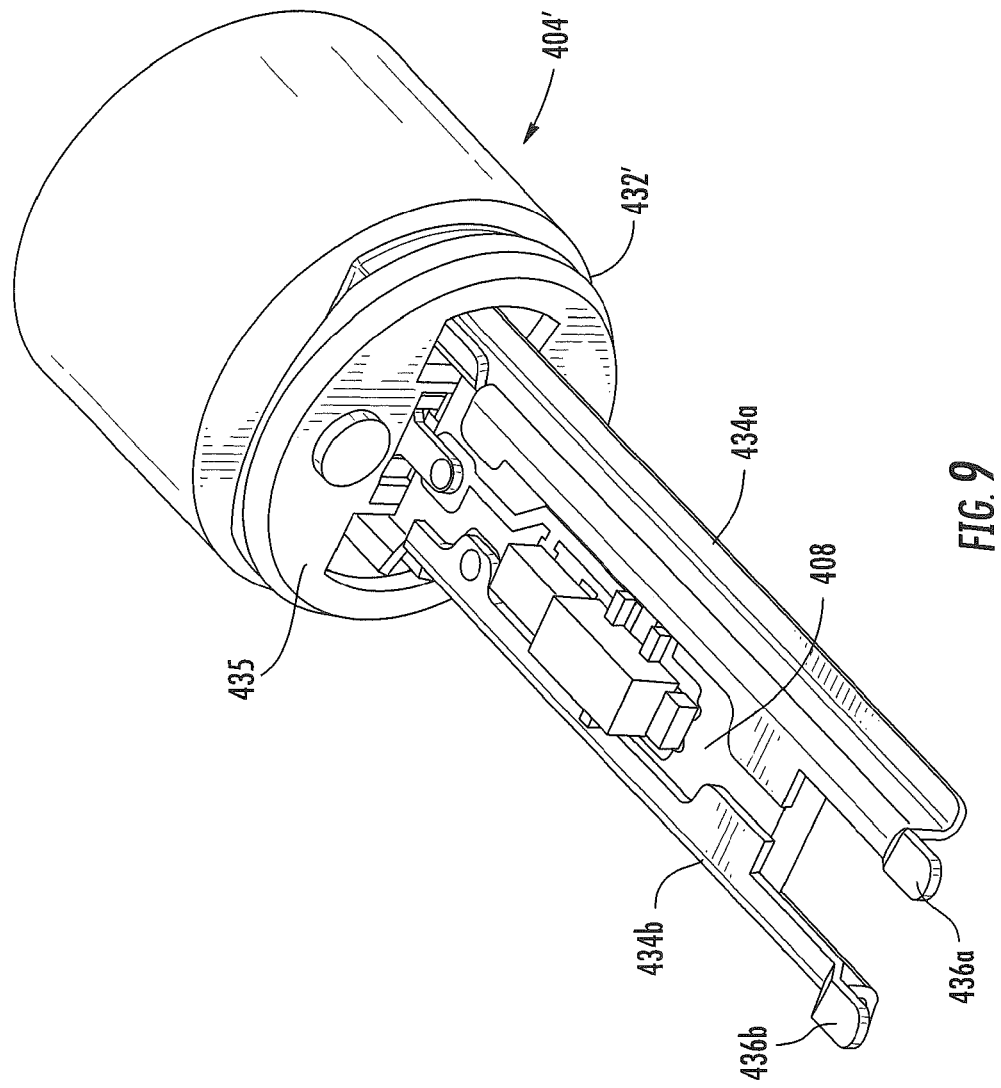

As illustrated in FIG. 9, the control component terminal 406 may couple to the electronic control component 408 such that an electrical connection is established therebetween. Accordingly, when the cartridge 400 is coupled to the control body 200, the electronic control component 408 may communicate therewith through the control component terminal 406. The electronic control component 408 may be configured to perform one or more of a variety of functions. Further, the electronic control component 408 may be configured as purpose-specific analog and/or digital circuitry with or without a processor, or the electronic control component may comprise hardware, software, or a combination of hardware and software. Accordingly, any or all of the functions performed by or in conjunction with the electronic control component 408 may be embodied in a computer-readable storage medium having computer-readable program code portions stored therein that, in response to execution by a processor, cause an apparatus to at least perform or direct the recited functions. In one particular instance, upon establishment of communication between the electronic control component 408 and the control body 200, the electronic control component may be configured to provide an authentication code or other appropriate indicia to the control body. In such instances, the control body 200 may be configured to evaluate the authentication indicia to determine whether the cartridge 400 is authorized for use with the control body. However, the electronic control component 408 may perform various other functions. Various examples of electronic control components and functions performed thereby are described in U.S. patent application Ser. No. 13/647,000, filed Oct. 8, 2012, which is incorporated herein by reference in its entirety.

As further illustrated in FIG. 9, a first heater terminal 434a and a second heater terminal 434b (collectively, "heater terminals 434"), which may comprise portions of the atomizer 412, may couple to a body end 435 of the base. Note that the base 404' illustrated in FIGS. 9 and 10 differs slightly from the embodiment of the base 404 described above. For example, the protrusions 432' define a differing configuration than the protrusions 432 described above. However, the protrusions 432' and other features of the base 404' perform substantially the same function in substantially the same manner. Accordingly, the base 404' is provided for purposes of illustrating an alternate embodiment only.

The heater terminals 434 may define a plurality of walls, which may extend at least partially around the electronic control component 408 in some embodiments such that the electronic control component is received therebetween. This configuration may allow the heater terminals 434 to provide support to the electronic control component 408, for example by contact therewith, such that the electronic control component is securely retained in place. Further, the heater terminals 434 may define first and second tabs 436a, 436b (collectively, "tabs 436"). The tabs 436 may be positioned at the end of the heater terminals 434 distal to the base 404'. In some embodiments the heater terminals 434 may be stamped or otherwise formed from a sheet of a metal material. However, the heater terminals 434 may be formed in various other manners and formed from any of a variety of conductive materials.

Figure 10:
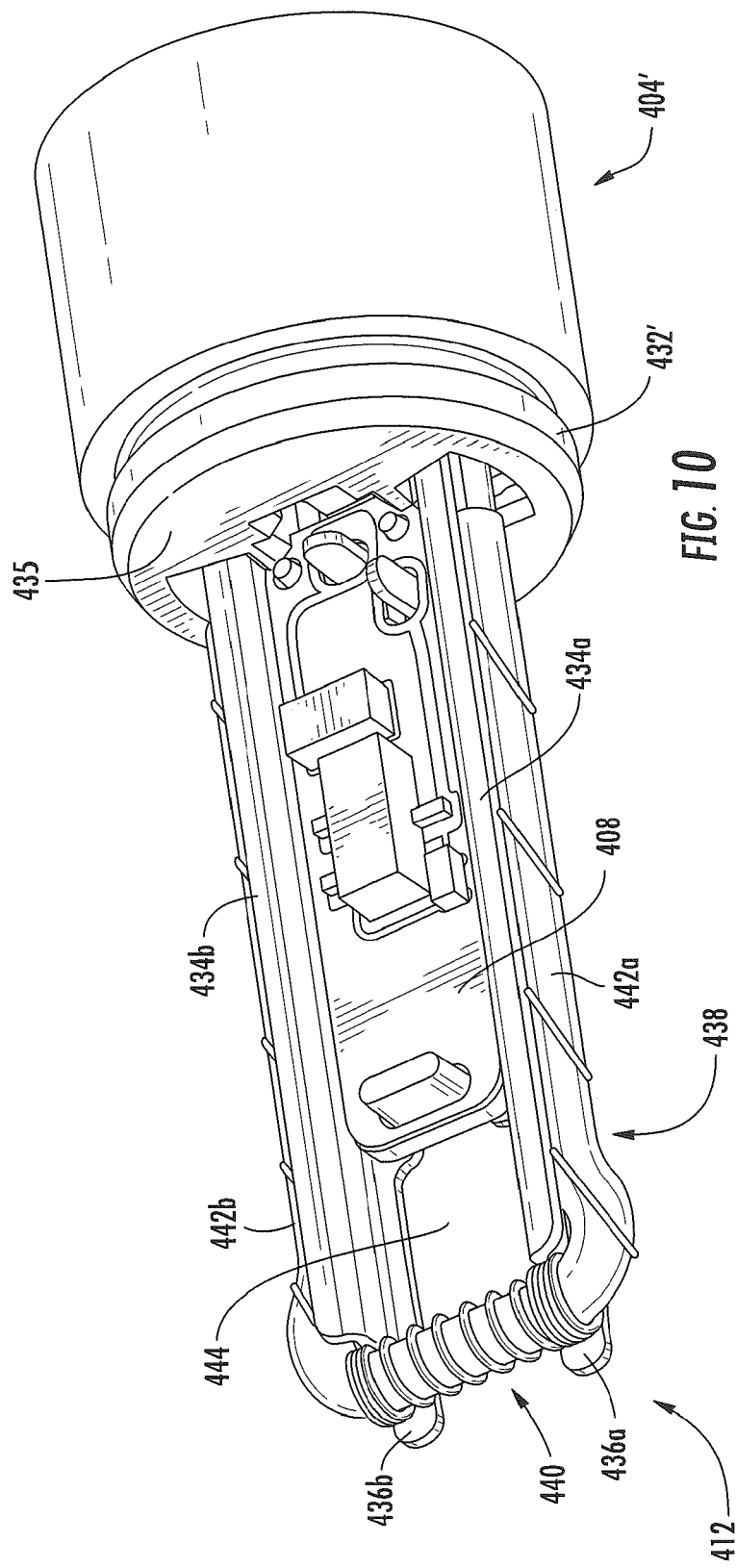

FIG. 10 illustrates the completed atomizer 412 coupled to the base 404' via the heater terminals 434. As illustrated in FIG. 10, in addition to the heater terminals 434, the atomizer 412 may further comprise a liquid transport element 438 and a heating element 440. The liquid transport element 438 and the heating element 440 may be configured in a substantially U-shaped configuration. The liquid transport element 438, which may comprise a wick (e.g., a fiberglass wick) in some embodiments, may be either preformed in the U-shaped configuration or bent to define this configuration. A first distal arm 442a and a second distal arm 442b (collectively, "distal arms 442") of the liquid transport element 438 may respectively extend along the first and second heater terminals 434a, 434b. Further a center section 442c of the liquid transport element 438 may extend between the heater terminals 434.

The liquid transport element 438 may comprise a bundle of fibers, such as fiberglass. In some embodiments, the liquid transport element 438 may comprise a braid of four or more fibers or yarns and thus define a braided wick. The liquid transport element 438 may be in the form of a sheath/core element. In particular, the sheath of the wick may be a braided wick as described above. The core of the wick may be a bundle of fibers, particularly twisted fibers. The liquid transport element specifically may comprise one or both of E-glass and C-glass.

The heating element 440 extends at least partially about the liquid transport element 438 and at least partially along the length of the liquid transport element. In some embodiments the heating element may terminate at the heater terminals 434 between which the heating element extends. However, in the illustrated embodiment the heating element 440 extends along substantially the entirety of the length of the liquid transport element 438.

In some embodiments, the heating element 440 may comprise a wire defining a plurality of coils wound about the liquid transport element 438, as illustrated in FIG. 10. The wire may comprise a material configured to produce heat when electrical current is provided therethrough. For example, the wire may comprise Kanthal (FeCrAl), Nichrome, Molybdenum disilicide ($MoSi_2$), molybdenum silicide (MoSi), Molybdenum disilicide doped with Aluminum ($Mo(Si,Al)_2$), or ceramic (e.g., a positive temperature coefficient ceramic) in some embodiments, although various other materials may be employed in other embodiments. In some embodiments the heating element 440 may be formed by winding the wire about the liquid transport element 438 as described in U.S. patent application Ser. No. 13/708,381, filed Dec. 7, 2012, which is incorporated herein by reference in its entirety. However, various other embodiments of methods may be employed to form the heating element 440, and various other embodiments of heating elements may be employed in the atomizer 208.

The tabs 436 may be configured to contact the heating element 440 such that an electrical connection is established therebetween. In this regard, the tabs 436 may be configured to be positioned adjacent to the heating element 440 such that the tabs directly contact one or more coils of the wire. Direct contact, as used herein, refers to physical contact between the heating element 440 and the heater terminals 434. However, direct contact, as used herein, also encompasses embodiments in which one or more welds couple the heating element 440 and the heater terminals 434. A weld, as used herein, refers to a solder, flux, braze, or other material that is deposited in liquid or molten form and hardens to form a connection. For example, a laser may be directed at a back side of the tabs 436, opposite from the heating element 440, which may weld the heating element to the tabs in order to provide for a connection therebetween.

As further illustrated in FIG. 10, in one embodiment the heating element 440 may define a variable coil spacing. The spacing of the coils may be the smallest proximate the tabs 436, greatest at the distal arms 442, and in between the spacing of the coils at the tabs and the distal arms between the heater terminals 434. By decreasing the spacing between the coils of the heating element 440 proximate the tabs 436, contact therebetween may be improved. The spacing of the coils of the heating element 440 between the tabs 436 may be selected to define a desired resistance and/or produce a desired amount of heat. Further, the spacing of the coils of the heating element 440 on the distal arms 442 of the liquid transport element 438 may be relatively large in order to decrease material costs associated with production of the heating element.

As noted above, the electronic control component 408 may be received between the heater terminals 434 and the distal arms 442 of the liquid transport element 438, which extend along the heater terminals. However, a gap 444 may be provided between the electronic control component 408 and the heating element 440. The gap 444 may reduce the amount of heat transferred to the electronic control component 408 from the heating element 440, for example by preventing direct conduction therebetween. Accordingly, the risk of damage to the electronic control component 408 from exposure to heat produced by the heating element 440 may be reduced.

Figure 11:
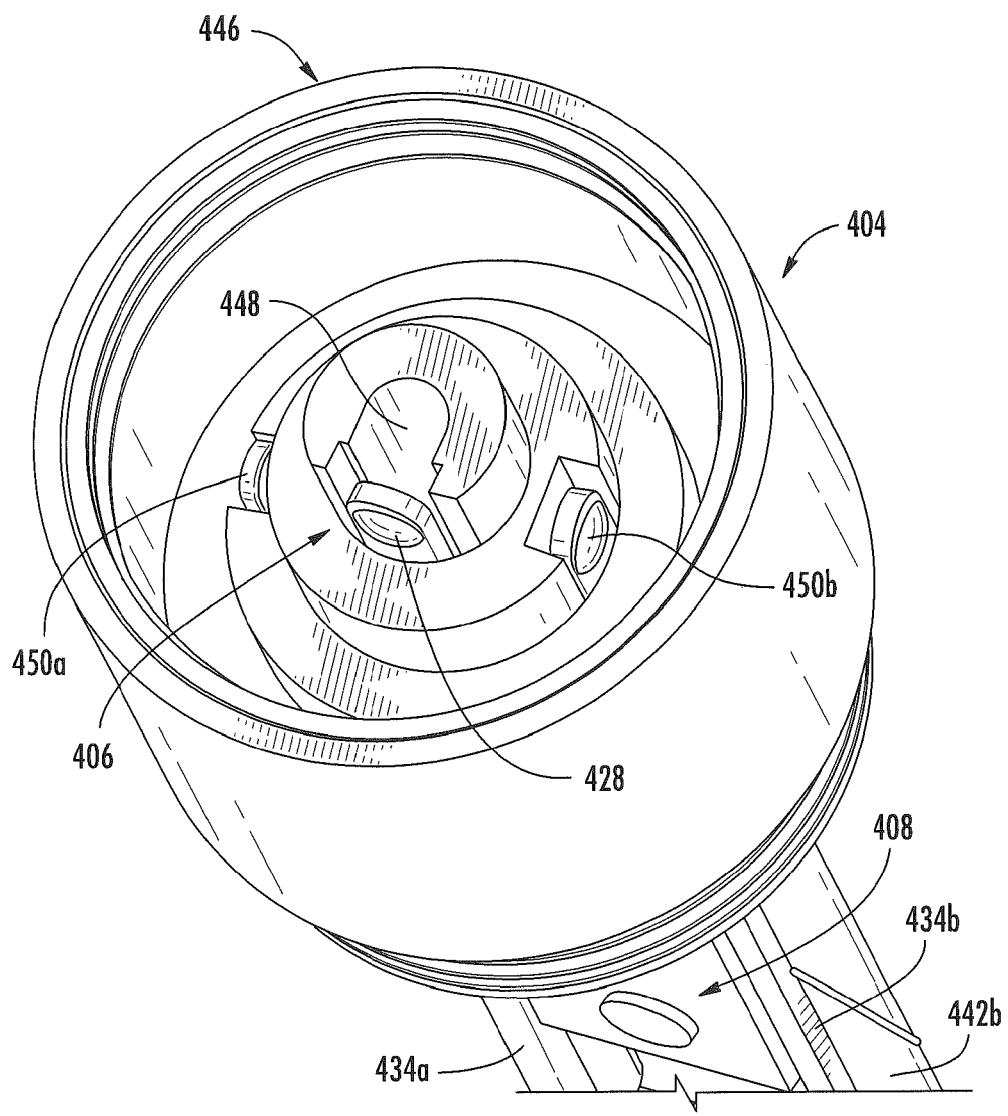

FIG. 11 illustrates an alternative perspective view of the assembly illustrated in FIG. 10, with the base 404' replaced with the base 404 for purposes of illustrating use of an alternate embodiment of a base. In particular, FIG. 11 illustrates a view of a connector end 446 of the base 404 configured to releasably engage the control body 200. As illustrated, a central opening 448 may be defined in the base 202. The central opening 448 may be configured to receive airflow therethrough from the control body 200 and direct the airflow toward the heating element 440 of the atomizer 412.

The heater terminals 434 may engage the base 404 and respectively extend to a first end 450a and a second end 450b (collectively, "ends 450"), which may be configured to engage the control body 200, so as to establish an electrical connection therewith. In this regard, as illustrated in FIG. 11, the end 428 of the control component terminal 406 and the ends 450 of the heater terminals 434 may be exposed at the connector end 446 of the base 404. The end 428 of the control component terminal 406 and the ends 450 of the heater terminals 434 may be located at differing positions within the base 404 such that they make connections with components at different locations within the control body, and avoid unintended contact therebetween.

In this regard, the end 428 of the control component terminal 406 and the ends 450 of the heater terminals 434 may be located at differing radial distances from the central opening 448. In the illustrated embodiment, the end 428 of the control component terminal 406 is located closest to the central opening 448, the first end 450a of the first heater terminal 434a is located farthest from the central opening, and the second end 450b of the first heater terminal 434b is located at a radial distance therebetween. Further, the end 428 of the control component terminal 406 and the ends 450 of the heater terminals 434 may extend to a plurality of different depths within the base 404. In the illustrated embodiment, the end 428 of the control component terminal 406 extends through the base 404 to a greatest depth, the first end 450a of the first heater terminal 434a extends through the base to the smallest depth, and the second end 450b of the second heater terminal 434b extends through the base to a depth therebetween.

Figure 12:
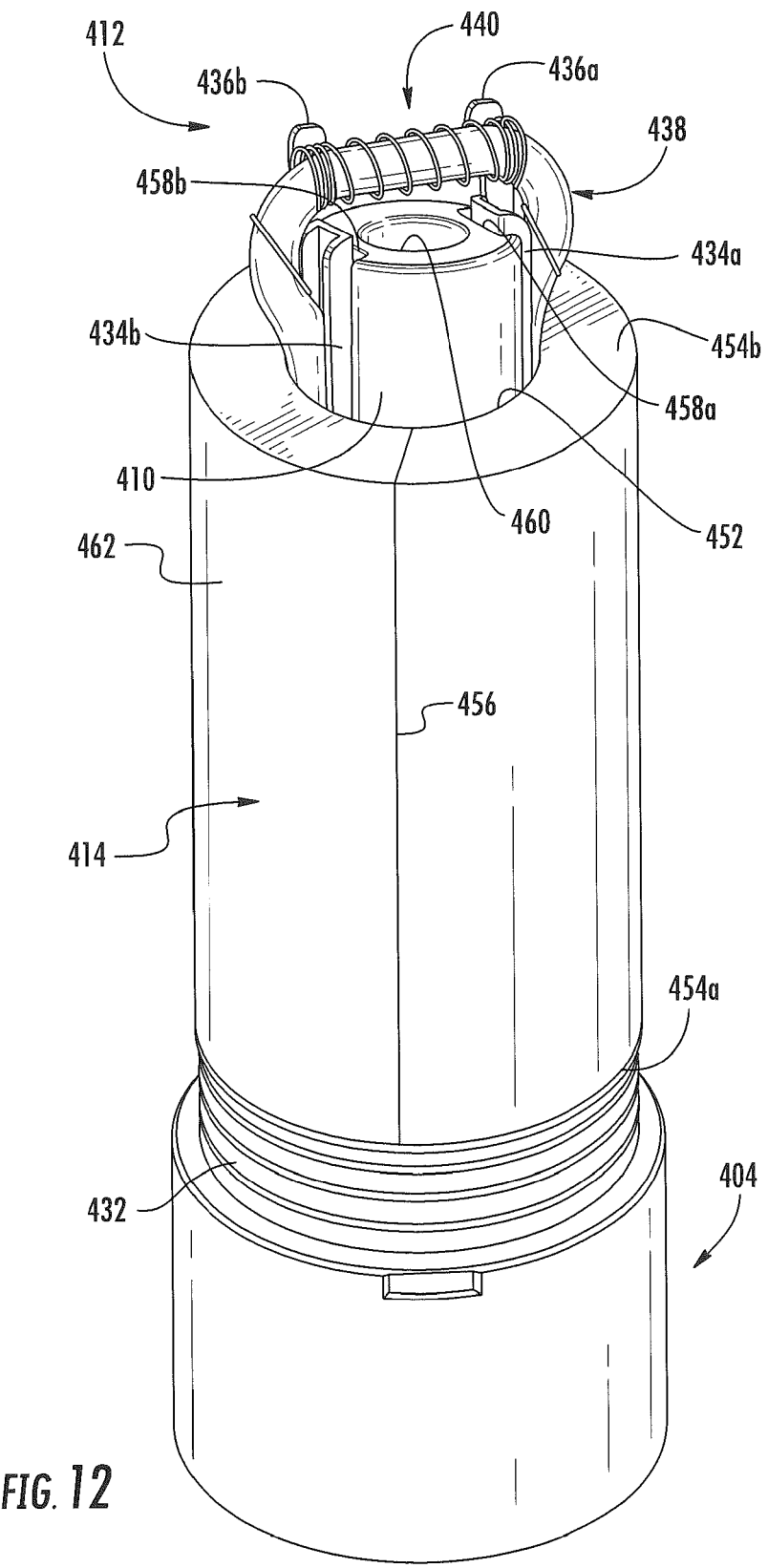

FIG. 12 illustrates a perspective view of the assembly of FIG. 11 after the reservoir substrate 414 is coupled thereto. The reservoir substrate 414 may be configured to hold an aerosol precursor composition. The aerosol precursor composition may comprise a variety of components including, by way of example, glycerin, nicotine, tobacco, tobacco extract, and/or flavorants. Various components that may be included in the aerosol precursor composition are described in U.S. Pat. No. 7,726,320 to Robinson et al., which is incorporated herein by reference.

The reservoir substrate 414 may define a cavity 452 extending therethrough from a first reservoir end 454a to a second reservoir end 454b (collectively, "reservoir ends 454"), wherein the first reservoir end is positioned proximate the base 404. In this regard, the reservoir substrate 414 may define a hollow tubular configuration. Note that although generally described herein as defining a hollow tubular configuration, the reservoir substrate 414 may define other shapes and configurations in other embodiments. The aerosol precursor composition may be retained within the material defining the reservoir substrate 414 itself, as opposed to within the cavity 452. This configuration may allow for airflow through the base 404, into and through the cavity 452, and past the heating element 440.

The reservoir substrate 414 can comprise one or more of various materials and can be formed in a variety of different manners. In one embodiment the reservoir substrate 414 can be formed from a plurality of combined layers that can be concentric or overlapping. For example, the reservoir substrate 414 can be a continuous sheet of a material that is rolled such that the ends thereof meet along a joint 456 to form the hollow tubular configuration, or multiple layers of the material may be wrapped thereabout. In other embodiments, the reservoir substrate 414 can be substantially a unitary component. For example, the reservoir substrate 414 can be shaped or molded so as to be a singular preformed element in the form of a substantially hollow tube, which may be substantially continuous in composition across the length and thickness thereof.

The reservoir substrate 414 can be formed from a material that is rigid or semi-rigid in some embodiments, while retaining the ability to store a liquid product such as, for example, an aerosol precursor composition. In certain embodiments, the material of the reservoir substrate 414 can be absorbent, adsorbent, or otherwise porous so as to provide the ability to retain the aerosol precursor composition. As such, the aerosol precursor composition can be characterized as being coated on, adsorbed by, or absorbed in the material of the reservoir substrate 414. The reservoir substrate 414 can be positioned within the cartridge 400 such that the reservoir substrate is in contact with the liquid transport element 438. More particularly, the reservoir substrate 414 can be manufactured from any material suitable for retaining the aerosol precursor composition (e.g., through absorption, adsorption, or the like) and allowing wicking away of the precursor composition for transport to the heating element 440.

The material of the reservoir substrate 414 may be suitable for forming and maintaining an appropriate shape. The material of the reservoir substrate 414 can be heat resistant so as to retain its structural integrity and avoid degradation at least at a temperature proximal to the heating temperature provided by the heating element 440. However, the reservoir substrate 414 need not be heat resistant to the full temperature produced by the heating element 440 due to the reservoir substrate being out of contact therewith. The size and strength of the reservoir substrate 414 may vary according to the features and requirements of the cartridge 400. In particular embodiments, the reservoir substrate 414 can be manufactured from a material suitable for a high-speed, automated manufacturing process. The reservoir substrate 414 may be a molded piece. According to one embodiment, the reservoir can be manufactured from a cellulose acetate tow which can be processed to form a hollow acetate tube. In particular, the reservoir may be a woven or non-woven fibrous mat comprising cellulose acetate and, optionally, a binder and/or fibers formed of a different material.

In certain embodiments, the reservoir substrate 414 can be provided in a form such that at least part of the cavity 452 is shaped and dimensioned to accommodate one or more other components of the cartridge 400. In some embodiments, the term "shaped and dimensioned" can indicate that a wall of the reservoir substrate 414 at the cavity 452 includes one or more indentations or protrusions that cause the interior of the reservoir substrate to have a shape that is other than substantially smooth and continuous. In other embodiments, the hollow nature of the reservoir substrate 414 can be sufficient to allow for accommodation of further components of the cartridge 400 without the need for formation of cavities or protrusions. Thus, the cartridge 400 can be particularly beneficial in that the reservoir substrate 414 can be pre-formed and can have a hollow interior defining the cavity 452 with a wall that is shaped and dimensioned to accommodate a further component of the cartridge in a mating arrangement. For example, the atomizer may define grooves configured to receive the atomizer. This particularly can facilitate ease of assembly of the cartridge 400 and can maximize the volume of the reservoir substrate 414 while also providing sufficient space for aerosol formation. However, in other embodiments the atomizer may define a substantially smooth interior surface and/or conform to the shape of the components which the atomizer contacts.

As illustrated in FIG. 12, the atomizer 412 may extend through the cavity 452 of the reservoir substrate 414 such that the heating element 440 is positioned proximate the second reservoir end 454*b*. More particularly, the atomizer 412 may extend through the cavity 452 such that the heating element 440 is positioned past the second reservoir end 454*b* and outside of the cavity. This embodiment may reduce the heat directly applied by the heating element 440 to the reservoir substrate 414 such that the amount of the aerosol precursor composition vaporized by the heating element is controlled in part by the flow of the aerosol precursor composition through the liquid transport element 438 to the heating element. Accordingly, the amount of aerosol precursor composition vaporized may be more precisely controlled. However, in other embodiments, it is not necessary for the atomizer to extend beyond the second reservoir end, and the atomizer can be positioned relative to the reservoir substrate such that the heating element is received within the cavity of the reservoir substrate.

As illustrated in FIGS. 6 and 12, in some embodiments the cartridge may additionally include a flow tube 410. As illustrated in FIG. 12, the flow tube 410 may be positioned between, and held in place by, the terminals 434. More particularly, the flow tube 410 may define first 458*a* and second 458*b* opposing grooves (collectively, "grooves 458"). The grooves 458 may be sized and shaped to respectively receive one of the terminals 434 therein. In this regard, in some embodiments the flow tube 410 may define a generally round outer perimeter, with the exception of the grooves 458. Thus, the flow tube 410 may be received inside the cavity defined through the reservoir substrate 410. Accordingly, the flow tube 410 may additionally or alternatively be held in place by the reservoir substrate 410. The flow tube 410 may also be held in place via contact with the electronic control component 408 in some embodiments.

The flow tube 410 may be configured to direct a flow of air received from the central opening 448 (see, e.g., FIG. 11) in the base 404 to the heating element 440 of the atomizer 412. More particularly, as illustrated in FIG. 12, the flow tube 410 may define a through hole 460 configured to receive air from the central opening 448 in the base 404 and direct it to the heating element 440. Accordingly, the size of the through hole 460 may be selected to define a desired velocity of air directed to the heating element 440. Accordingly, a desired amount of aerosol may be delivered to the air as the air passes the heating element 440. For example, the through hole 460 may taper from a relatively larger diameter to a relatively smaller diameter proximate the heating element 440. However, in other embodiments the through hole 490 may define a substantially constant diameter.

In some embodiments the flow tube 410 may comprise a ceramic material. For example, the flow tube 410 may comprise 96.5% aluminum trioxide in one embodiment. This material may provide heat resistance which may be desirable due to proximity to the heating element 440. However, the flow tube 410 may be formed from various other materials in other embodiments.

Figure 13:
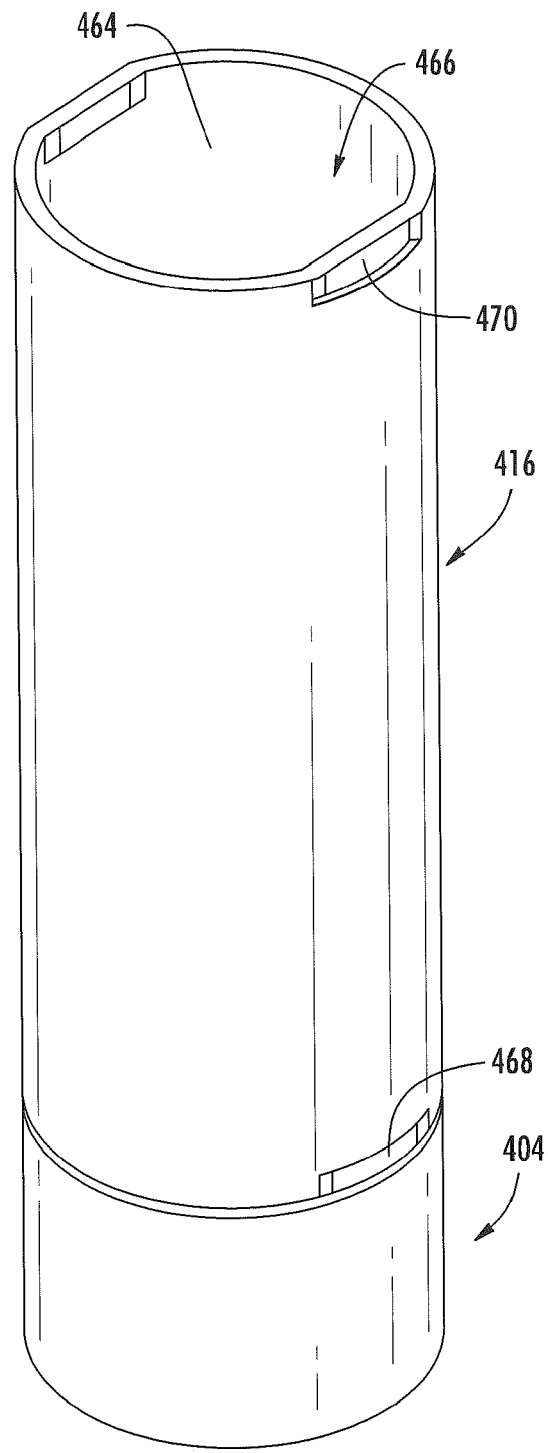

The reservoir substrate 414 includes an exterior surface 462 that can be substantially shaped and adapted to conform to an interior surface 464 of the external shell 416 (see, FIG. 13). In this regard, the external shell 416 may define a tubular shape with a cavity 466 extending therethrough sized to receive the reservoir substrate 414. For example, an inner radius of the external shell 416 may substantially correspond to, or may be slightly larger than, an outer radius of the reservoir substrate 414. Accordingly, the external shell 416 may be received over the reservoir substrate 414 and coupled to the base 404, as illustrated in FIG. 13. One or more indentations 468 may engage the threads or protrusions 432 on the base 404 such that coupling is retained therebetween.

Figure 14:
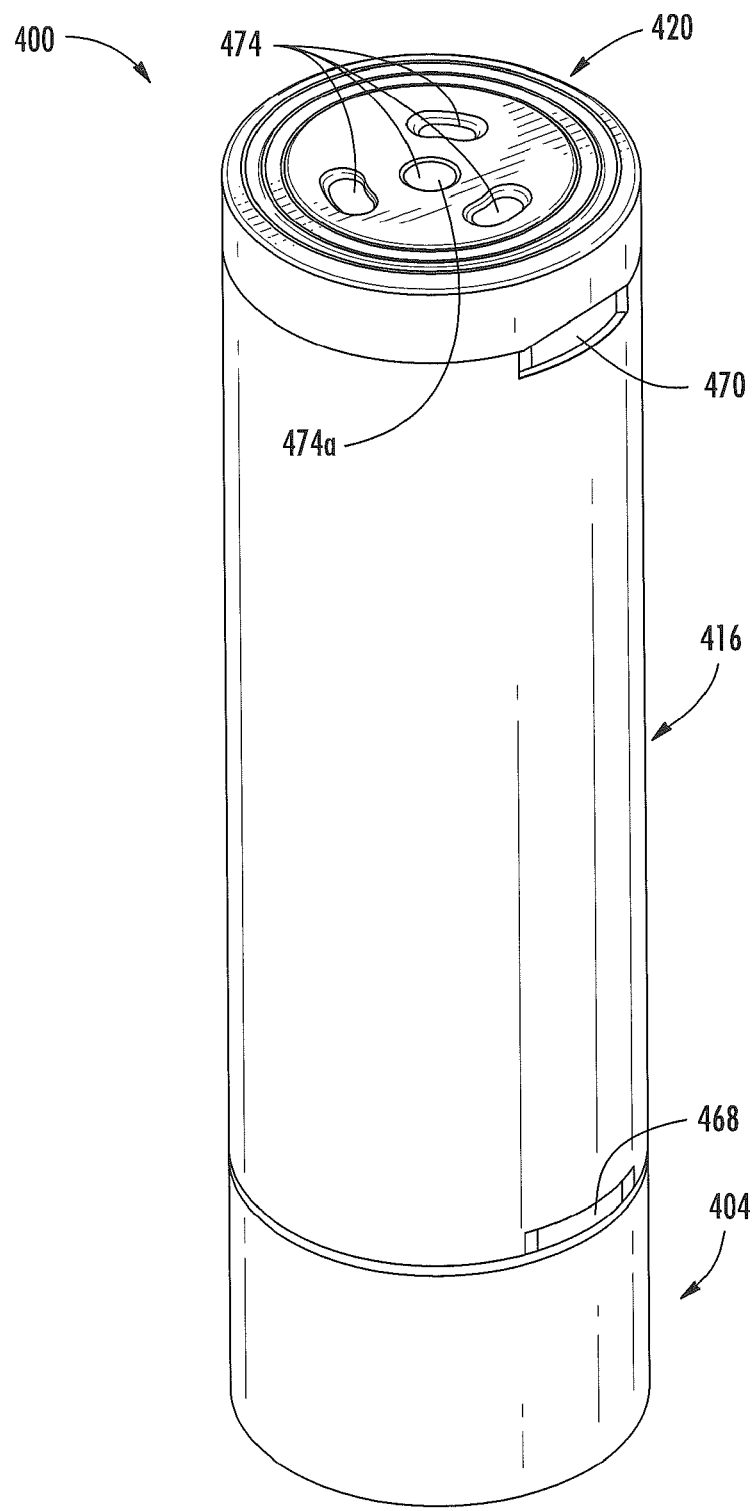

As illustrated in FIG. 14, the external shell 416 may couple to the mouthpiece 420 such that the cavity 466 defined by the external shell is at least partially enclosed. More particularly, in one embodiment one or more indentations 470 may engage threads or protrusions 472 on the mouthpiece 420 (see, FIG. 6) such that coupling therebetween is retained. The mouthpiece 420 defines one or more openings 474 through which air mixed with aerosol produced by the atomizer 412 may be directed when a user draws on the mouthpiece, as described in accordance with the above-noted example embodiments of smoking articles. The mouthpiece shipping plug 422 (see, FIG. 6) may engage one or more of the openings 474 such as a center opening 474*a* prior to use of the cartridge 400 in order to prevent entry of contaminants through the openings 474 in the mouthpiece 420.

Figure 15:
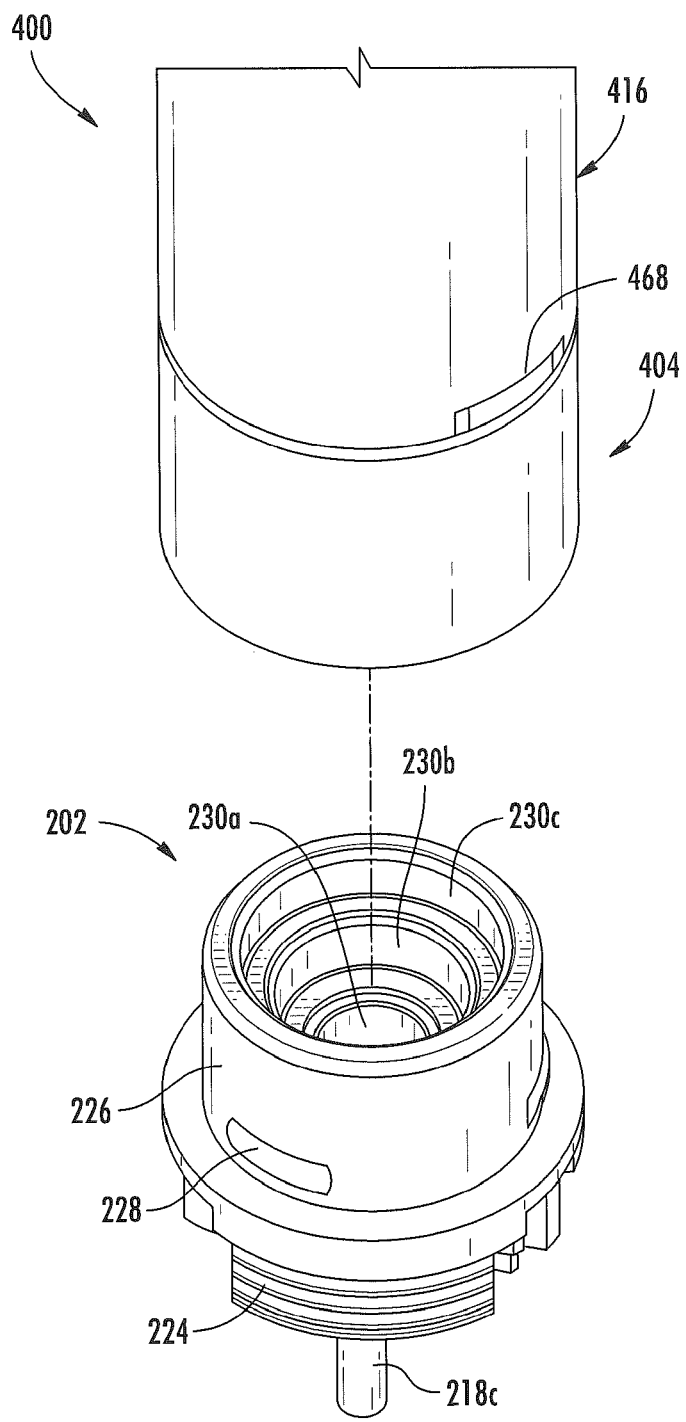
Figure 16:
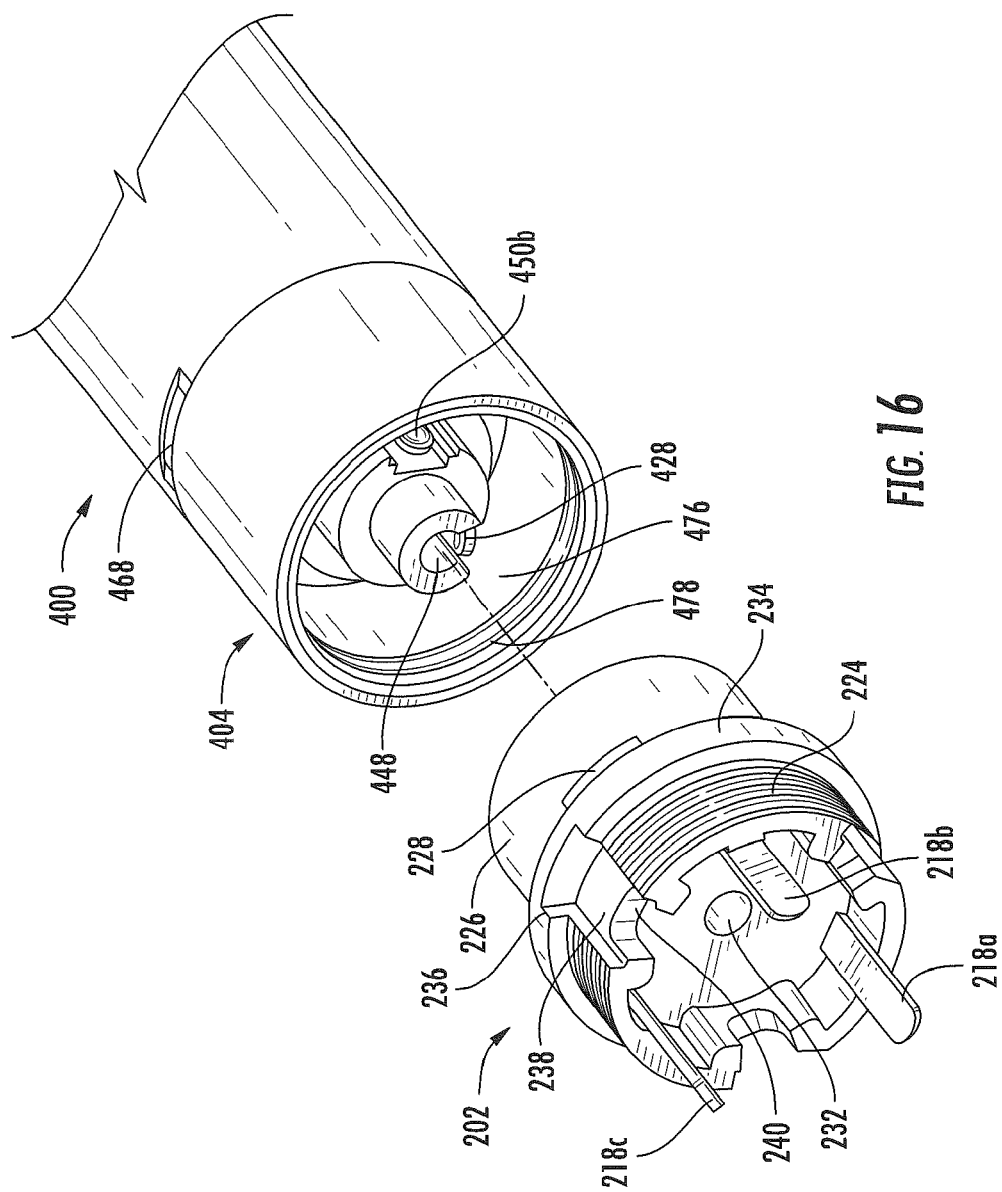
FIG. 16 illustrates an opposing second partial perspective view of the cartridge of FIG. 6 and the coupler of FIG. 15.

FIGS. 15 and 16 illustrate an enlarged view of the coupler 202, which may comprise a portion of the control body 200, aligned with the cartridge 400. The coupler 202 may be configured to engage the base 404 of the cartridge 400 and various other embodiments of cartridges as described herein. As illustrated, the coupler 202 may comprise protrusions or threads 224 that are configured to engage the outer tube 214 of the control body 200 such that a mechanical connection is formed therebetween.

The coupler 202 may define an outer periphery 226 configured to mate with an inner periphery 476 of the base 404. In one embodiment the inner periphery 476 of the base 404 may define a radius that is substantially equal to, or slightly greater than, a radius of the outer periphery 226 of the coupler 202. Further, the coupler 202 may define one or more protrusions 228 at the outer periphery 226 configured to engage one or more recesses 478 defined at the inner periphery 476 of the base 404. However, various other embodiments of structures, shapes, and components may be employed to couple the base 404 to the coupler 202. In some embodiments the connection between the base 404 of the cartridge 400 and the coupler 202 of the control body 200 may be substantially permanent, whereas in other embodiments the connection therebetween may be releasable such that, for example, the control body may be reused with one or more additional cartridges.

The coupler 202 may further comprise a plurality of electrical contacts 230*a-c* respectively configured to contact the end 428 of the control component terminal 406 and the ends 450 of the heater terminals 434. The electrical contacts 230*a-c* may be positioned at differing radial distances from a central opening 232 through the coupler 202 and positioned at differing depths within the coupler. The depth and radius of each of the electrical contacts 230*a-c* is configured such that the end 428 of the control component terminal 406 and the ends 450 of the heater terminals 434 respectively come into contact therewith when the base 404 and the coupler 202 are joined together to establish an electrical connection therebetween. More particularly, in the illustrated embodiment, a first electrical contact 230a defines the smallest diameter, a third electrical contact 230c defines the greatest diameter, and a second electrical contact 230b defines a diameter therebetween. Further, the electrical contacts 230a-c are located at differing depths within the connector 202 relative to a connector end thereof. In the illustrated embodiment, the first electrical contact 230a is located at a greatest depth, the third electrical contract 230c is located at the smallest depth, and the second electrical contact 230b is located at a depth therebetween. The first electrical contact 230a may be configured to contact the end 428 of the control component terminal 406, the second electrical contact 230b may be configured to contact the second end 450b of the second heater terminal 434b, and the first end 450a of the first heater terminal 450a may be configured to contact the third electrical contact 230c.

In the illustrated embodiment the electrical contacts 230a-c comprise circular metal bands of varying radii positioned at differing depths within the coupler 202 as described above. In one embodiment the bands may comprise continuous round rings. In another embodiment, the bands may comprise a sheet of metal material that is wound into the circular configuration and defines a joint where the ends thereof meet. In some embodiments the joint between the ends of each band of metal material may be configured at opposing non-perpendicular angles relative to a longitudinal length of the metal material defining the bands. Thereby, the ends of the band may meet at a joint that does not extend parallel to a central axis extending through the coupler 202. This configuration may be preferable in that it avoids creating a joint extending parallel to the central axis through the coupler 202, which could form a poor connection with an end of one of the heater terminals or the control component terminal when in contact therewith. Each of the bands defines a major contact surface facing radially inwardly toward the central axis of the coupler 202. The bands defining the electrical contacts 230a-c are separated from one another by stepped surfaces of the body of the coupler 202, which may be oriented perpendicularly to the radially facing major surfaces of the electrical contacts.

When the electrical contacts 230a-c comprise circular bands and the end 428 of the control component terminal 406 and the ends 450 of the heater terminals 434 extend to corresponding depths and radii within the base 404, electrical connections between the base and the coupler 202 may be established regardless of the rotational orientation of the base with respect to the coupler. Accordingly, connection between the base 404 of the cartridge 400 and the coupler 202 of the control body may be facilitated. The electrical contacts 230a-c may be respectively coupled to a plurality of control body terminals 218a-c that connect to a plurality of components within the control body 200 such as the electrical power source 212 and the control component 208 therefore. In contrast, existing embodiments of aerosol delivery devices may employ electrical contacts in the threads of the connectors. Such connectors may be subject to wear from use, due to the rotation contact therebetween necessarily occurring when the connectors are threaded together.

Further, when the base 404 of the cartridge 400 and the coupler 202 of the control body 200 are coupled together, a fluid connection may also be established. In this regard, the coupler 202 may define a fluid pathway configured to receive air from an ambient environment and direct the air to the cartridge 400 when a user draws thereon. More particularly, in one embodiment the coupler 202 may define a rim 234 with a radially extending notch 236 defined therein. Further a longitudinally extending recessed slot 238 may extend from the notch 236 to an opening 240. The opening 240 may define a cutout or a hole through a portion of the coupler in some embodiments. Thus, when the coupler 202 is engaged with the end of the outer body 214 of the control body 200, the fluid pathway through the notch 236, the slot 238, and the opening 240 may remain open. Air drawn through this path may then be directed through the central opening 232 of the coupler 202 and the central opening 448 of the base 404 when the coupler and the base are connected to one another. Thus, air may be directed from the control body 200 through the cartridge 400 in the manner described above when a user draws on the mouthpiece 420 of the cartridge.

Accordingly, the above-described cartridge 400 may provide benefits in terms of ease of assembly and ease of attachment to the coupler 202 of the control body 200. In particular, with respect to the cartridge 400, assembly thereof may be simplified in that the components thereof may be generally axially assembled. More specifically, in one embodiment the control component terminal 406 may be coupled to the base 404, the electronic control component 408 may be coupled to the control component terminal, the heater terminals 434 may be coupled to the base, the flow tube 410 may be coupled to the heater terminals and the electronic control component, the heating element 440 may be coupled to the liquid transport element 438 and the combination thereof may be coupled to the heater terminals to form the atomizer 412, the reservoir substrate 414 may be coupled to the atomizer, the external shell 416 may be coupled to the base, and the mouthpiece 420 may be coupled to the external shell. The label 418 (see, FIG. 6) may be coupled to the external shell 416 in some embodiments. Further, the base shipping plug 402 (see, FIG. 6) may be coupled to the inner periphery 476 of the base 404 in some embodiments to protect the base during transport and storage.

Figure 17:
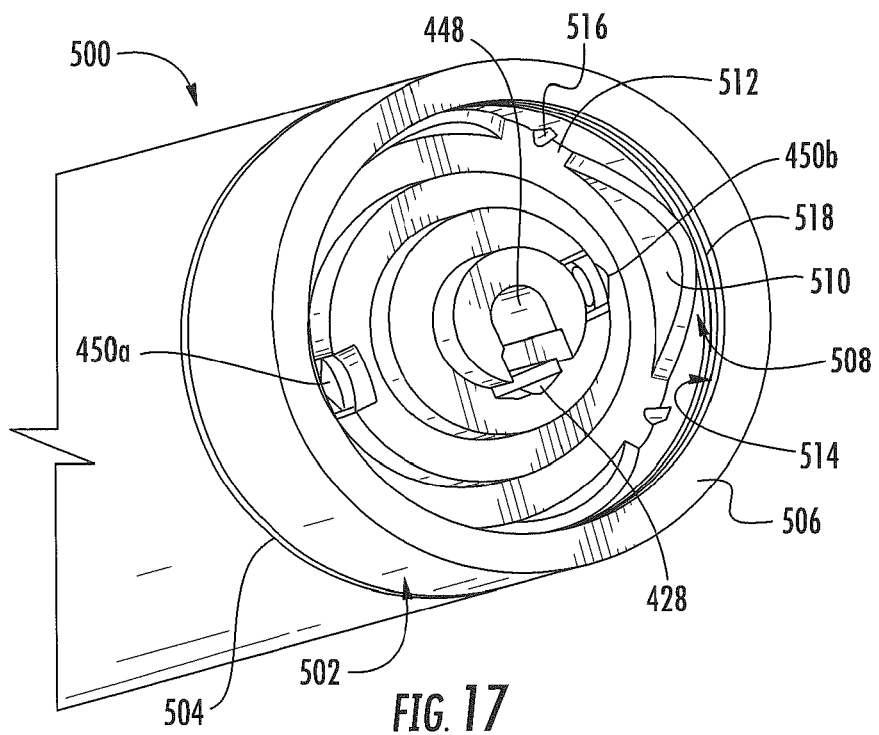
FIG. 17 illustrates a perspective view of a cartridge including a base with an anti-rotation mechanism according to an additional example embodiment of the present disclosure.

Although FIGS. 15 and 16 illustrate embodiments of a base and a coupler for a cartridge and a control body, various other embodiments of these components may be provided. In this regard, FIG. 17 illustrates a cartridge 500, which may comprise some or all of the cartridge components described above, and an alternate embodiment of a base 502. The base 502 may extend between a body end 504 oriented toward components of the cartridge 500 such as a reservoir substrate and an atomizer, and a connector end 506 configured to releasably engage a control body. The base 502 may include some of the features and components described above, including, for example, the end 428 of a control component terminal, the end of the heater terminals 450, and the central opening 448 extending therethrough.

The base 502 may further comprise an anti-rotation mechanism 508 at the connector end 506. The anti-rotation mechanism 508 may be configured to prevent rotation of the cartridge 500 relative to a control body when engaged therewith. In contrast, some prior art embodiments of cartridges may rely on threaded connections to mate with corresponding control bodies. However, the potential for cross-threading therebetween exists, which may damage one or both of the control body and the cartridge. Further, users may prefer a connection between a cartridge and a control body that feels substantially permanent. In this regard, the anti-rotation mechanism 508 may be employed to provide a connection between the cartridge 500 and a control body that feels secure and permanent to an end user despite the releasability thereof. Additionally, prevention of rotation may reduce wear on the electrical contacts in the control body.

As illustrated in FIG. 17, the anti-rotation mechanism 508 may comprise a plurality of protrusions 510 and a plurality of recesses 512 alternatingly disposed about an inner periphery 514 of the base 502. As further illustrated in FIG. 17, a width of each of the protrusions 510 may increase from the connector end 506 toward the body end 504 of the base 502. Conversely, a width of each of the recesses 512 may decrease from the connector end 506 toward the body end 504 of the base 502. The base 502 may further comprise a plurality of ribs 516 extending from the inner periphery 514 of the base 500 at the recesses 512, the purpose of which will be described below.

Figure 18:
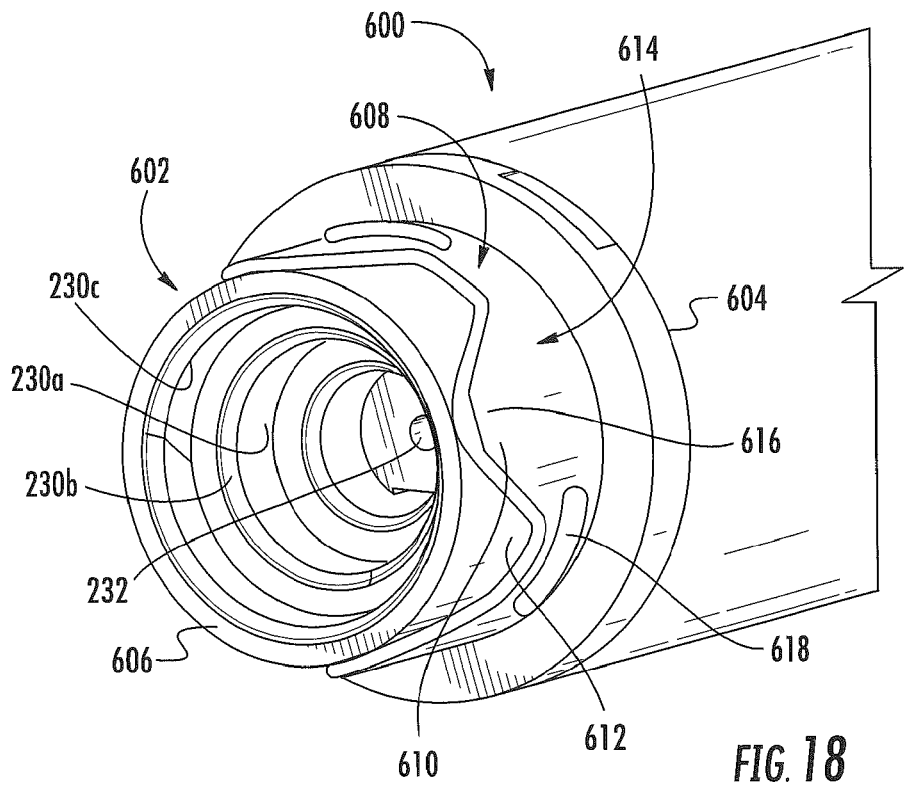
FIG. 18 illustrates a perspective view of a control body including a coupler with an anti-rotation mechanism according to an additional example embodiment of the present disclosure.

FIG. 18 illustrates a control body 600, which may comprise some or all of the control body components described above, and an alternate embodiment of a coupler 602. The coupler 602 may extend between a body end 604 oriented toward components of the control body 600 such as a control component and an electrical power source, and a connector end 606 configured to releasably engage a cartridge. The coupler 602 may include some of the features and components described above, including, for example, the electrical contacts 230a-c, and the central opening 232.

The coupler 602 may further comprise an anti-rotation mechanism 608 at the connector end 606. The anti-rotation mechanism 608 may be configured to prevent rotation of the control body 600 relative to a cartridge when engaged therewith. In contrast, some prior art embodiments of control bodies rely on threaded connections to mate with corresponding cartridges. However, as noted above, the potential for cross-threading therebetween exists, which may damage one or both of the control body and the cartridge and users may prefer a connection between a cartridge and a control body that feels substantially permanent. In this regard, the anti-rotation mechanism 608 may be employed to provide a connection between the control body 600 and a cartridge that feels secure and permanent to an end user despite the releasability thereof, and which may reduce wear on electrical contacts of the coupler caused by rotation between the cartridge and the control body.

As illustrated in FIG. 18, the anti-rotation mechanism 608 may comprise a plurality of protrusions 610 and a plurality of recesses 612 alternatingly disposed about an outer periphery 614 of the coupler 602. As further illustrated in FIG. 18, a width of each of the protrusions 610 may increase from the connector end 606 toward the body end 604 of the coupler 602. Conversely, a width of each of the recesses 512 may decrease from the connector end 606 toward the body end 604 of the coupler 602.

Figure 19:
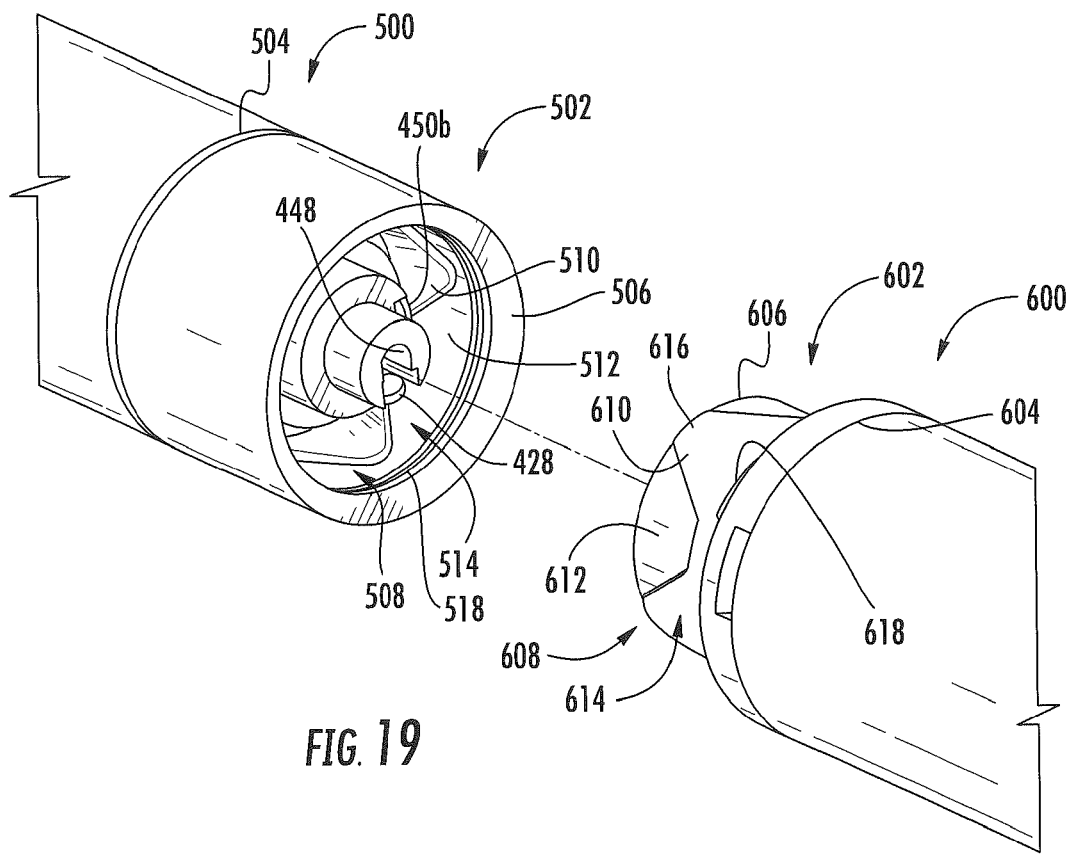
FIG. 19 illustrates alignment of the cartridge of FIG. 17 with the control body of FIG. 18.

The base 502 of the cartridge 500 illustrated in FIG. 17 may be configured to engage the coupler 602 of the control body 600 illustrated in FIG. 18. In this regard, FIG. 19 illustrates an alignment of the base 502 and the coupler 602 which may be employed during coupling between the cartridge 500 and the control body 600. As illustrated, the cartridge 500 may be axially aligned with the control body 600.

During coupling of the cartridge 500 to the control body 600, the outer periphery 614 of the coupler 602 may engage the inner periphery 514 of the base 502. Accordingly, the protrusions 510 and the recesses 512 of the base 502 may engage the recesses 612 and the protrusions 610 of the coupler 602. Initially, when a user axially aligns the cartridge 500 and the control body 600, the protrusions 610 of the coupler 602 may not be aligned with the recesses 512 of the base 502 and the recesses 612 of the coupler may not be aligned with the protrusions 510 of the base.

As noted above, the widths of the protrusions 510, 610 may increase extending away from the respective connector ends 506, 606. Further, the widths of the recesses 610, 612 may decrease in width extending away from the respective connector ends 506, 606. Accordingly, even if protrusions 512 of the base 502 initially contact the protrusions 612 of the coupler 602, the protrusions may deflect from one another and enter respective recesses 512, 612.

Figure 20:
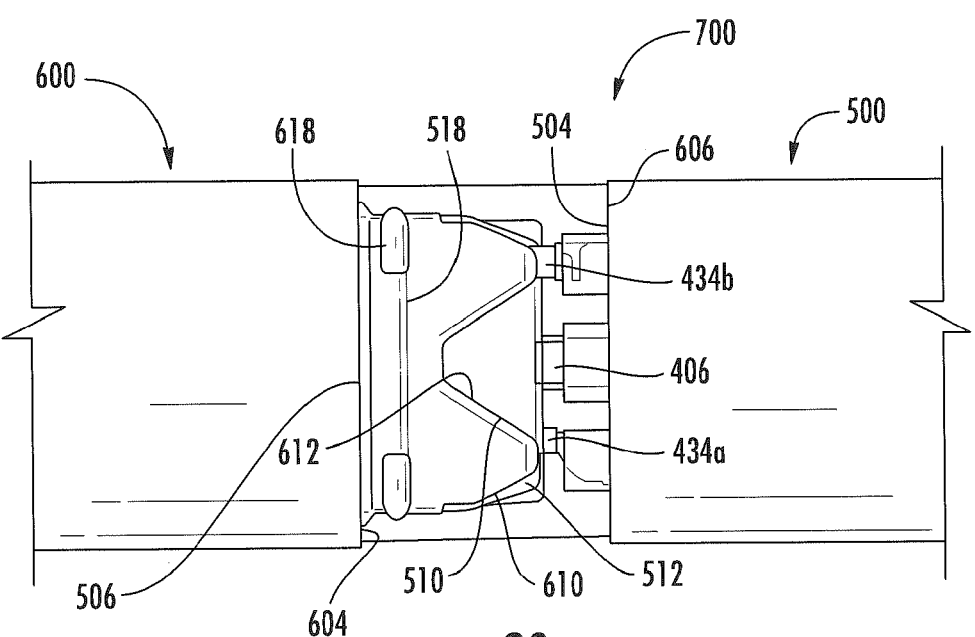
FIG. 20 illustrates an aerosol delivery device comprising the cartridge of FIG. 17 and the control body of FIG. 18 with a modified view through the aerosol delivery device illustrating the engagement of the anti-rotation mechanism of the cartridge with the anti-rotation mechanism of the connector body.

FIG. 20 illustrates an aerosol delivery device 700 comprising the cartridge 500 and the control body 600. More particularly, FIG. 20 includes a modified view through the aerosol delivery device 700 illustrating the engagement of the anti-rotation mechanism 508 of the cartridge 500 with the anti-rotation mechanism 608 of the connector body 600. As illustrated, in some embodiments a radial dimension of the inner periphery 514 of the base 502 decreases from the connector end 506 toward the body end 504. Conversely, a radial dimension of the outer periphery 614 of the coupler 602 increases from the connector end 606 toward the body end 604. Changes in the radial dimensions of the inner periphery 514 of the base 502 and the outer periphery 614 of the coupler 602 as described above may facilitate alignment and attachment of the cartridge 500 to the control body 600. However, in other embodiments the inner periphery 514 of the base 502 and the outer periphery 614 of the coupler 602 may define substantially constant radial dimensions extending from the respective connector end 506, 606 toward the respective body end 504, 604.

When brought into contact in the manner described above, the base 502 of the cartridge 500 may engage the coupler 602 of the control body 600 to form the aerosol delivery device 700, as illustrated in FIG. 20. Further, the anti-rotation mechanisms 508, 608 may engage one another such that relative rotational motion between the cartridge 500 and the control body 600 is substantially prevented. In particular, engagement between the edges of the protrusions 512, 612 may substantially prevent rotational movement between the cartridge 500 and the control body 600.

Further, during connection of the cartridge 500 to the control body 600, tips 616 of the protrusions 610 of the coupler 602 may engage the ribs 516 extending from the inner periphery 514 of the base 500 at the recesses 512. In one embodiment the ribs 516 may be wedge-shaped and extend further toward the center of the base 502 at an end thereof closest to the body end 504 of the base. Accordingly, as the coupler 602 extends into the base 502, the ribs 516 may deform due to contact with the tips 616 of the protrusions 610 of the coupler 602. For example, in one embodiment the base 502 may be formed from a material that is softer than a material defining the coupler 602. Alternatively or additionally, contact between the ribs 516 and the tips 616 of the protrusions 610 of the coupler 602 may center the control body 602 with respect to the base 502. Accordingly, the ribs 516 may improve the connection between the cartridge 500 and the control body 600.

In some embodiments, as illustrated in FIGS. 17, 19, and 20, the base 502 may further comprise a groove 518 extending at least partially around the inner periphery 514 thereof. Additionally, the coupler 602 may further comprise one or more circumferential protrusions 618 extending at least partially around the outer periphery thereof. The circumferential protrusions 618 may engage the groove 518 in the base such that the base 502 is releasably engaged with the coupler 602. Accordingly, the cartridge 500 and the control body 600 may "snap" into releasable engagement. The cartridge 500 may be decoupled from the control body 600 by grasping both the cartridge and the control body and pulling the cartridge and the control body axially away from one another. In contrast, use of a threaded connection, as may be employed in other embodiments of aerosol delivery devices, may require unthreading the cartridge from the control body, which may take more time, and the strength required to decouple the cartridge from the control body may vary depending on how tight the cartridge was initially screwed to the control body, resulting in an inconsistent user experience.

Note that in other embodiments the anti-rotation mechanism of the cartridge may be positioned at an outer surface thereof. Conversely, the anti-rotation mechanism of the control body may be positioned at an inner surface thereof. Accordingly, it should be understood that the particular embodiment of the cartridge and the control body described herein is provided by way of example only, and various other configurations may be employed.

Other embodiments of bases and couplers configured to engage one another that include anti-rotation mechanisms are also provided. By way of example, FIGS. 21 and 22 respectively illustrate embodiments of a base 802 and a coupler 902 configured to engage one another. The base 802 may comprise a portion of a cartridge and the coupler 902 may comprise a portion of a control body as described above.

Figure 21:
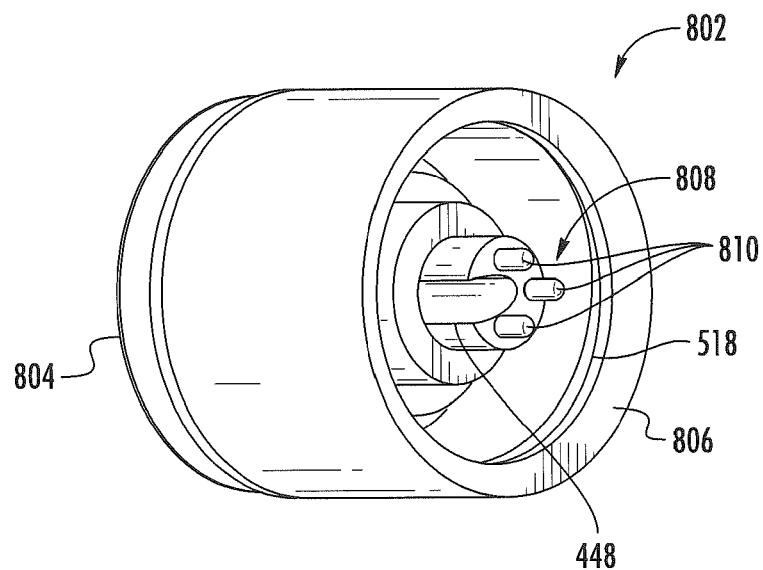
FIG. 21 illustrates a perspective view of a base with an anti-rotation mechanism according to an additional example embodiment of the present disclosure.

In this regard, the base 802 illustrated in FIG. 21 may comprise some or all of the components described above. The base 802 may extend between a body end 804 configured to be oriented toward other components of a cartridge such as a reservoir substrate and an atomizer, and a connector end 806 configured to releasably engage a control body. Further, the base 802 may include a central opening 448 and a groove 518 as described above. Although the base 802 is illustrated in isolation, the base may also include a control component terminal and heater terminals extending therethrough when assembled with additional components of a cartridge. The base 802 may further comprise an anti-rotation mechanism 808 at the connector end 806. The anti-rotation mechanism 808 may be configured to prevent rotation of a cartridge relative to a control body when engaged therewith.

Figure 22:
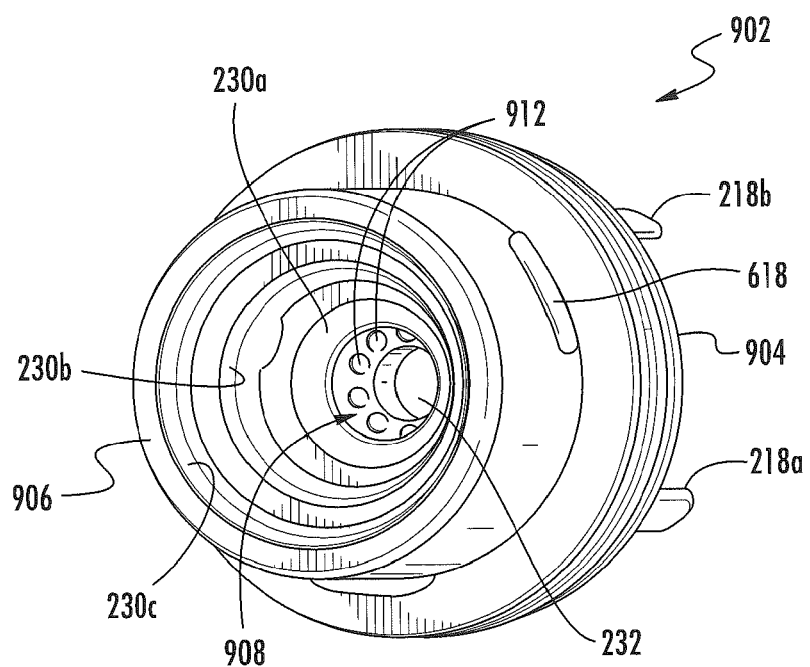
FIG. 22 illustrates a perspective view of a coupler with an anti-rotation mechanism according to an additional example embodiment of the present disclosure.

The coupler 902 illustrated in FIG. 22 may comprise some of the components of the couplers described above, including, for example, the electrical contacts 230*a-c*, the central opening 232, and the control body terminals 218. The coupler 902 may extend between a body end 904 configured to be oriented toward components of a control body such as a control component and an electrical power source, and a connector end 906 configured to releasably engage a cartridge. The coupler 902 may further comprise an anti-rotation mechanism 908 at the connector end 906. The anti-rotation mechanism 908 may be configured to prevent rotation of a control body relative to a cartridge when engaged therewith.

More particularly, the anti-rotation mechanism 808 of the base 802 may comprise a plurality of protrusions 810 (e.g., prongs) and the coupler 902 may include a plurality of recesses 912 configured to receive the protrusions. As illustrated, the protrusions 810 and the recesses 912 may respectively at least partially surround the central openings 448, 232 through the base 802 and the coupler 902. In one embodiment, as illustrated, the coupler 902 may include more recesses 912 than protrusions 810 defined by the base. Accordingly, the recesses 912 of the coupler 902 may be configured to receive the protrusions 810 of the base in multiple rotational configurations. In another embodiment the prongs 810 and the recesses 912 may be spaced apart from one another at differing distances such that the base 802 and the coupler 902 are keyed to join in one or more of a limited number of defined rotational orientations.

Figure 23:
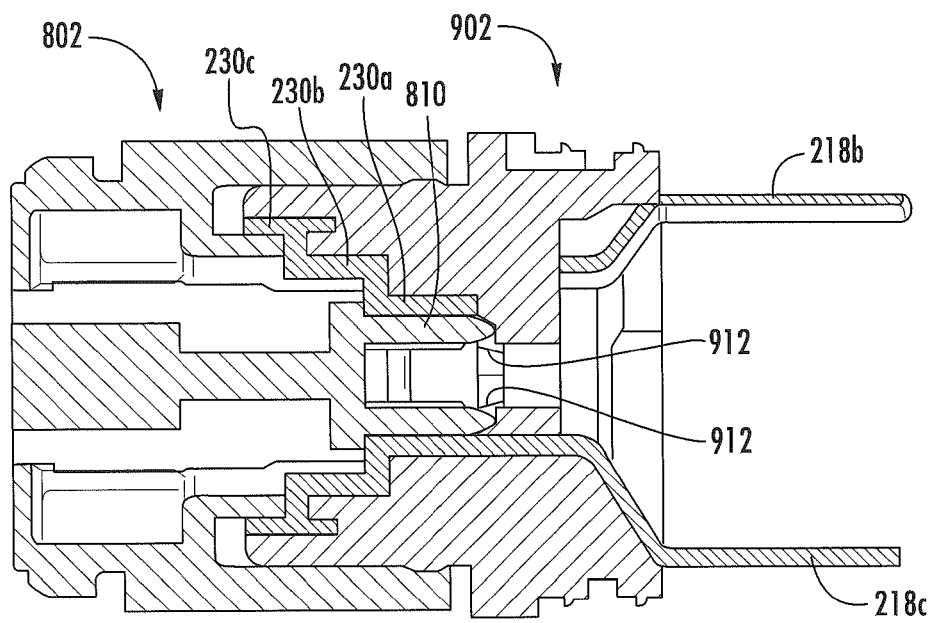
FIG. 23 illustrates a sectional view through the base of FIG. 21 and the coupler of FIG. 22 in an engaged configuration.

FIG. 23 illustrates the base 802 engaged with the coupler 902. As illustrated, when the base 802 is engaged with the coupler 902, the protrusions 810 may extend into the recesses 912. Thus, engagement between the protrusions 810 and the recesses 912 may substantially prevent rotation of the base 802 relative to the coupler 902.

Accordingly, FIGS. 21-23 illustrate alternate embodiments of anti-rotation mechanisms that may be employed with embodiments of cartridges, control bodies, and aerosol delivery devices according to embodiments of the present disclosure. However, as noted above, various other embodiments of anti-rotation mechanisms are also provided. For example, the protrusions may extend from the coupler and the recesses may be provided in the base in an alternate embodiment. Further, it should be understood that the features and components of the various embodiments of components described herein may be combined in a variety of manners. Thus, the various features and components described herein are illustrated in separate features merely for example purposes.

Figure 24:
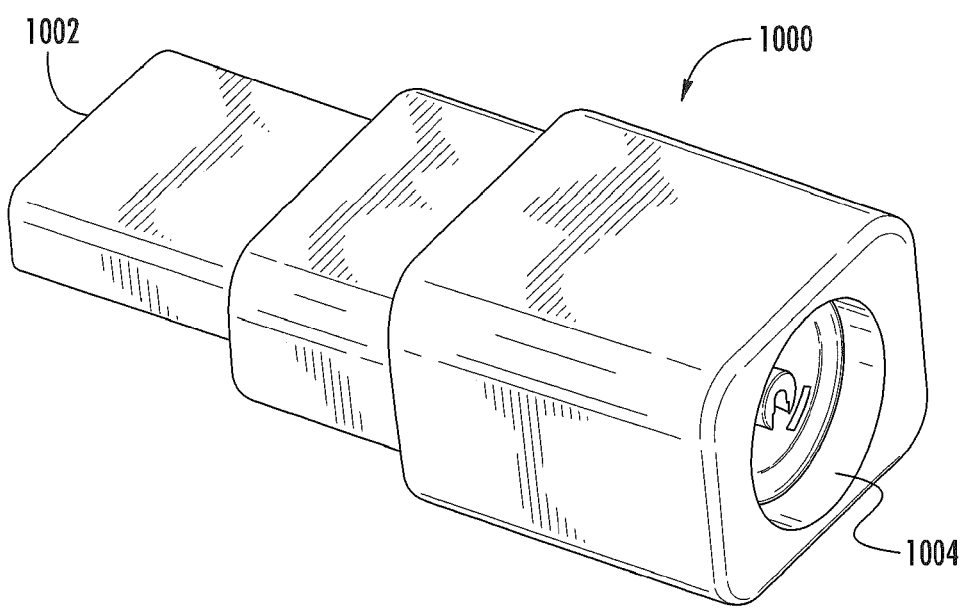
FIG. 24 illustrates an adaptor according to an example embodiment of the present disclosure.
Figure 25:
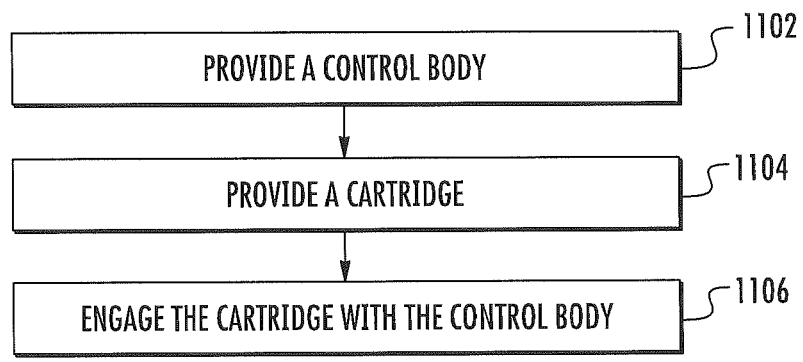
FIG. 25 illustrates a method for forming an aerosol delivery device according to an example embodiment of the present disclosure.

As briefly noted above, in some embodiments the control bodies described herein may be rechargeable. In this regard, FIG. 24 illustrates an embodiment of an adaptor 1000. The adaptor 1000 may include a USB connector 1002 at one end and a control body connector 1004 at an opposing end. The control body connector 1004 may be configured to match the shape of a base of a cartridge to which a control body is configured to engage. Thus, when the USB connector 1002 of the adaptor 1000 is plugged into an appropriate receptacle and the control body connector 1004 is plugged into a control body, the electrical power source (e.g., a battery) of the control body may be charged.

A method for forming an aerosol delivery device is also provided. As illustrated in FIG. 2, the method may comprise providing a control body at operation 1102. In some embodiments the control body may comprise a control component, an electrical power source, a coupler extending between a body end oriented toward the control component and the electrical power source and a connector end comprising an anti-rotation mechanism, and/or any other components as described herein. Further, the method may include providing a cartridge at operation 1104. In some embodiments the cartridge may comprise a reservoir substrate configured to hold an aerosol precursor composition, an atomizer configured to atomize the aerosol precursor, a base extending between a body end oriented toward the reservoir substrate and the atomizer and a connector end comprising an anti-rotation mechanism, and/or any other components as described herein. Additionally, the method may include engaging the connector end of the base to the connector end of the coupler such that the cartridge releasably engages the control body and the anti-rotation mechanism of the control body engages the anti-rotation mechanism of the cartridge to substantially prevent rotation of the cartridge relative to the control body at operation 1106.

In some embodiments of the method, engaging the connector end of the base to the connector end of the coupler at operation 1106 may comprise engaging a plurality of protrusions and a plurality of recesses alternatingly disposed about an inner periphery of the base of the cartridge with a plurality of protrusions and a plurality of recesses alternatingly disposed about an outer periphery of the control body.

Engaging the connector end of the base to the connector end of the coupler at operation 1106 may further comprise engaging a plurality of ribs extending from the inner periphery of the base at the recesses with the protrusions of the control body. Additionally, engaging the connector end of the base to the connector end of the coupler at operation 1106 may further comprise engaging a circumferential protrusion extending at least partially around the outer periphery of the coupler with a groove extending at least partially around the inner periphery of the base.

Figure 26:
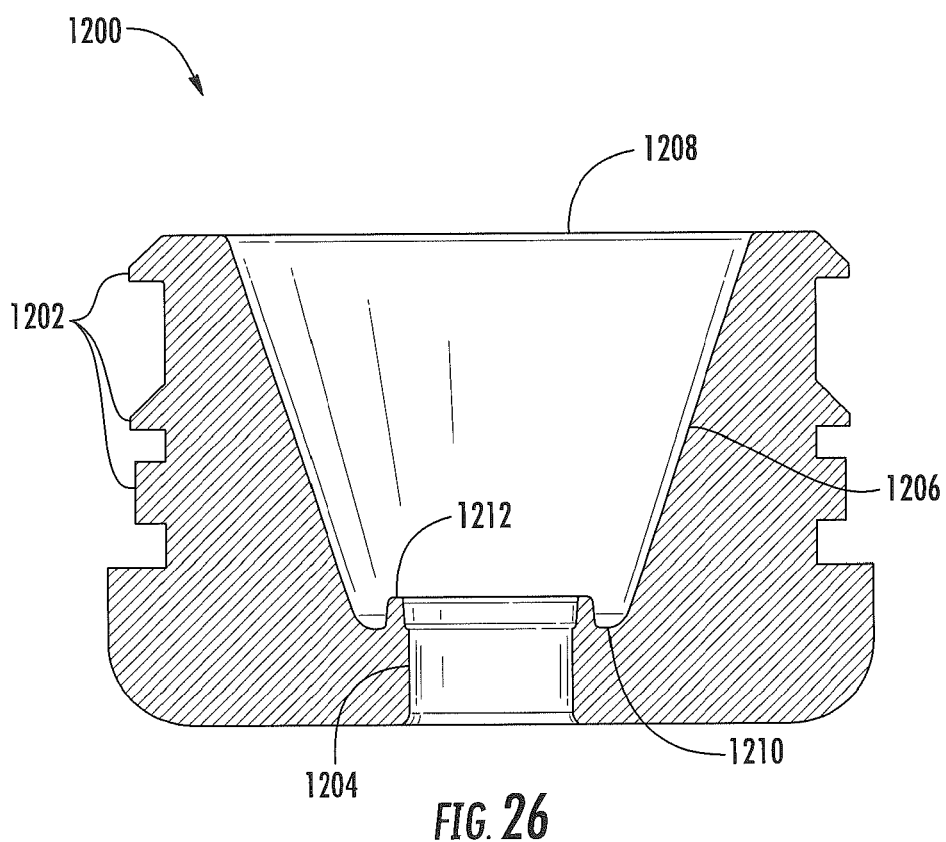
FIG. 26 illustrates a cross-sectional view through a funneled mouthpiece according to an example embodiment of the present disclosure.

FIG. 26 illustrates a cross-sectional view through an additional example embodiment of a mouthpiece 1200 for a cartridge. The mouthpiece 1200 may include one or more protrusions 1202 configured to engage an external shell or outer body of a cartridge such that the mouthpiece is coupled therewith. The mouthpiece 1200 may include one or more openings through which a user may draw air mixed with aerosol produced by an atomizer when a user draws on the mouthpiece. In this regard, the illustrated embodiment of the mouthpiece 1200 includes a single central external opening 1204 defining by through hole.

As illustrated, the mouthpiece 1200 defines a funnel section 1206 in communication with the external opening 1204. The funnel section 1206 may be defined by an integral interior surface of the mouthpiece 1200 in some embodiments, as illustrated. More specifically, the funnel section 1206 extends from a major end 1208 to a minor end 1210, wherein the minor end defines a smaller cross-sectional area than the major end. The minor end 1210 of the funnel section 1206 may be positioned proximate the external opening 1204. Accordingly, air drawn through the mouthpiece 1200 may enter through the major end 1208 of the funnel section 1206, travel to the minor end 1210 of the funnel section, and exit to a user's mouth through the external opening 1204. In some embodiments a lip 1212 may be defined at the minor end 1210 of the funnel section 1206. The lip 1212 and the funnel section 1206 are configured to improve airflow through a cartridge to which the mouthpiece 1200 is attached by reducing eddy currents occurring downstream of the heating element. In this regard, although not intending to be limited by any particular theory, the lip 1212 and/or the funnel section 1206 may function as a velocity stack. Note that the mouthpiece 1200 may be employed in any of the embodiments of cartridges disclosed herein.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A cartridge for an aerosol delivery device, the cartridge comprising:
 a reservoir configured to hold an aerosol precursor composition;
 an atomizer configured to atomize the aerosol precursor, the atomizer comprising a plurality terminals; and
 a base extending between a body end oriented toward the reservoir and the atomizer and a connector end configured to releasably engage a control body, the base comprising an anti-rotation mechanism at the connector end configured to prevent rotation of the cartridge relative to the control body when engaged therewith, the terminals extending to a plurality of ends positioned within the base to electrically couple the cartridge to the control body.

2. The cartridge of claim 1, wherein the anti-rotation mechanism comprises a plurality of protrusions and a plurality of recesses alternatingly disposed about an inner periphery of the base.

3. The cartridge of claim 2, wherein a width of each of the protrusions increases from the connector end toward the body end and a width of each of the recesses decreases from the connector end toward the body end.

4. The cartridge of claim 2, further comprising a plurality of ribs extending from the inner periphery of the base at the recesses.

5. The cartridge of claim 2, wherein a radial dimension of the inner periphery of the base decreases from the connector end toward the body end.

6. The cartridge of claim 2, wherein the base further comprises a groove extending at least partially around the inner periphery thereof.

\* \* \* \* \*